US007781463B2

(12) United States Patent
Gil et al.

(10) Patent No.: US 7,781,463 B2
(45) Date of Patent: Aug. 24, 2010

(54) ENZYME INHIBITORS

(75) Inventors: Ana Martinez Gil, Madrid (ES); Ana Castro Morera, Madrid (ES); Maria Concepcion Martin Perez, Madrid (ES); Mercedes Alonso Cascon, Madrid (ES); Isabel Dorronsoro Diaz, Madrid (ES); Francisco Jose Moreno Munoz, Madrid (ES); Francisco Wandosell Jurado, Madrid (ES)

(73) Assignees: Consejo Superior de Investigaciones Cientificas, Madrid (ES); Universidad Autonoma de Madrid (UAM), Madrid (ES)

( * ) Notice: Subject to any disclaimer, the term of this patent is extended or adjusted under 35 U.S.C. 154(b) by 243 days.

(21) Appl. No.: 11/788,755

(22) Filed: Apr. 20, 2007

(65) Prior Publication Data
US 2008/0033012 A1 Feb. 7, 2008

Related U.S. Application Data

(60) Division of application No. 10/917,175, filed on Aug. 12, 2004, now Pat. No. 7,666,885, which is a division of application No. 10/290,569, filed on Nov. 8, 2002, now Pat. No. 6,872,737, which is a continuation-in-part of application No. PCT/GB01/02100, filed on May 11, 2001.

(30) Foreign Application Priority Data

May 11, 2000 (ES) .............................. 200001185
Dec. 12, 2000 (GB) .............................. 0030284.4

(51) Int. Cl.
  *A61K 31/41* (2006.01)
  *C07D 285/08* (2006.01)
(52) U.S. Cl. .................. 514/361; 514/351; 548/128; 548/129
(58) Field of Classification Search ............. 548/128, 548/129; 514/361, 351
  See application file for complete search history.

(56) References Cited

U.S. PATENT DOCUMENTS

| 2,863,803 | A | 12/1958 | Benghiat et al. |
| 3,374,240 | A | 3/1968 | Ottman et al. |
| 3,534,057 | A | 10/1970 | Krenzer |
| 3,900,485 | A | 8/1975 | Krenzer |
| 4,183,816 | A | 1/1980 | Gavin et al. |
| 6,872,737 | B2 | 3/2005 | Gil et al. |
| 7,265,259 | B2 | 9/2007 | Perez et al. |
| 7,531,561 | B2 | 5/2009 | Padilla et al. |
| 2005/0222220 | A1 | 10/2005 | Padilla et al. |

FOREIGN PATENT DOCUMENTS

| DE | 2109755 | 9/1972 |
| DE | 4420522 | 12/1995 |
| EP | 0 711 773 A1 | 5/1996 |
| EP | 04075997.9 | 4/2004 |
| GB | 1115350 | 5/1968 |
| JP | S48-44432 | 6/1973 |
| JP | 58216177 | 12/1983 |
| WO | WO 95/17182 | 6/1995 |
| WO | WO 00/21927 | 4/2000 |
| WO | WO 00/38675 | 7/2000 |
| WO | WO 01/09106 A1 | 2/2001 |

OTHER PUBLICATIONS

Alonso et al., "GSK-Inhibitors: Discoveries and Developments", Current Medicinal Chemistry, 2004, 11, pp. 755-763.
Cascon, Mercedes Alonso, "Tesis Doctoral: Farmacos Modificadores De La Enfermedad De Alzheimer: 1,2,4-Tiadiazolidin-3,5-Dionas (TDZDs) Primeros Inhibidores ATP-NO Competitivos De GSK-3β", Universidad De Madrid, 2003, chapters 1 and 5.
Martinez et al., "First Non-ATP Competitive Glycogen Synthase Kinase 3 β (GSK-3 β) Inhibitors: Thiadiazolidinones (TDZD) as Potential Drugs for the Treatment of Alzheimer's Disease", J./ Med. Chem., 2002, 45, pp. 1292-1299.
Martinez et al., "Glycogen Synthase Kinase 3 (GSK-3) Inhibitors as New Promising Drugs for Diabetes, Neurodegeneration, Cancer and Inflammation", Medicinal Research Reviews, 2002, 22, No. 4, pp. 373-384.
USPTO Issue Notification in U.S. Appl. No. 11/098,610, mailed Apr. 22, 2009, 1 page.
Response to Rule 312 Communication—Entered in U.S. Appl. No. 11/098,610, mailed Apr. 6, 2009, King & Spaling, LLP; Amendment under 37 C.F.R. §1.312, Response to Interview Summary and Issue Fee Payment—Entered—in U.S. Appl. No. 11/098,610, 6 pages.

(Continued)

*Primary Examiner*—Rei-tsang Shiao
(74) *Attorney, Agent, or Firm*—Fish & Richardson P.C.

(57) ABSTRACT

Compounds of general formula (I):

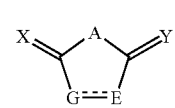

(I)

where A, E, G, X, Y and the bond - - - take various meanings are of use in the preparation of a pharmaceutical formulation, for example in the treatment of a disease in which GSK-3 is involved, including Alzheimer's disease or the non-dependent insulin diabetes mellitus, or hyperproliferative disease such as cancer, displasias or metaplasias of tissue, psoriasis, arteriosclerosis or restenosis.

10 Claims, No Drawings

OTHER PUBLICATIONS

King & Spalding, LLP; PTOL -85, Correction of Entity Status and Payment of Fee Deficiency, Amendment under 37 C.F.R. §1.312 in U.S. Appl. No. 11/098,610, filed Mar. 27, 2009, 10 pages.

Notice of Allowance, Determination of Patent Term Adjustment, Notice of Allowability, Interview Summary, Examiner's Amendment and Reasons for Allowance in U.S. Appl. No. 11/098,610, mailed Dec. 15, 2008, 10 pages.

King & Spalding, LLP; Amendment and Response to Office Action mailed May 16, 2008 in U.S. Appl. No. 11/098,610, filed Oct. 16, 2008, 43 pages.

Non-Final Office Action for U.S. Appl. No. 11/098,610 mailed May 16, 2008, 6 pages.

Kramer & Amado, P.C.; Request for Continued Examination and Amendments for in U.S. Appl. No. 11/098,610, filed Mar. 26, 2008, 19 pages; Rule 132 Declaration of Miguel Medina Padilla, dated Mar. 14, 2009, 7 pages.

Final Office Action for U.S. Appl. No. 11/098,610, mailed Sep. 27, 2007, 6 pages.

Kramer & Amado, P.C.; Amendment to Office Action mailed Jan. 26, 2007 for U.S. Appl. No. 11/098,610, filed Jul. 25, 2007, 16 pages.

Office Action for U.S. Appl. No. 11/098,610, mailed Jan. 26, 2007, 9 pages.

Kramer & Amado, P.C.; Preliminary Amendment and Response to Restriction and Election of Species Requirement for U.S. Appl. No. 11/098,610, filed Dec. 29, 2006, 10 pages.

Restriction Requirement for U.S. Appl. No. 11/098,610, mailed Nov. 2, 2006, 8 pages.

Restriction Requirement for U.S. Appl. No. 11/788,755, mailed Jan. 15, 2009, 10 pages.

Fish & Richardson PC; Response to Restriction Requirement for U.S. Appl. No. 11/788,755, filed Apr. 15, 2009, 3 pages.

Non-Final Office Action for U.S. Appl. No. 11/788,755, mailed Jul. 13, 2009, 11 pages.

Eghtessad et al., "Uber die Reaktion von Benzylisothiocyanat mit Glyoxal-di(tert-butylnitron)", Arch. Pharm. (Weinheim) 373, 357-361, 1980, Abstract.

English-translated version of DE 4420522, and a comment from USPTO Germanic language translator, dated May 4, 2004.

Groutas et al., 1994, "Substituted 3-oxo-1,2,5,-thiadiazolidine 1, 1-dioxides..", CAS:120:124451.

Heuer et al., 1996, "Bactericidal thiadiazolidinedione.", CAS:124:48317.

Jha et al., 1998, "Donor behavior of isoperthiocyanic acid..", CAS:128:96805.

Marcinkeviciene et al., 2000, Biochemical Pharmacology, "Selective inhibition of bacterial dihydroorotate..", 60:339-342.

Martinez et al., "Arylimino-1,2,4-Thiadiazolidinones: A New Family of Potassium Channel Openers", *Bioorganic & Medicinal Chemistry*, vol. 5, No. 7, pp. 1275-1283 (1997).

Martinez et al., "Synthesis and Potential Muscarinic Receptor Binding and Antioxidant Properties of 3-(Thiadiazolyl)pyridine 1-Oxide Compounds" *Arch. Pharm. Pharm. Med. Chem.*, vol. 332, pp. 191-194 (1999).

Slomczynska et al., "Efficient Synthesis of 1,2,4—Dithiazolidine-3,5-diones (Dithiasuccinoyl-amines) and Observation on Formation of 1,2,4—Thiadiazolidine-3,5-diones by Related Chemistry", *J. Heterocyclic Chem.*, vol. 21, pp. 241-246 (1984).

Bao et al., "Glycogen Synthase Kinase-3β Inhibition Attenuates Asthma in Mice", AJRCCM Articles in Press, published Jun. 7, 2007 as dio:10.1164/rccm.200609-1292OC.

Collino et al., "Treatment with Glycogen Synthase Kinase-3β Inhibitor, TDZD-8, Affects Transient Cerebral Ischemia/Reperfusion Injury in the Rat Hippocampus", Shock, 2008, pp. 1-10.

Cuzzocrea et al., "Glycogen Synthase Kinase-3β Inhibition Reduces Secondary Damage in Experimental Spinal Cord Trauma", JPET Fast Forward, published on Apr. 6, 2006 as DOI:10.1124/jpet.106.102863.

Cuzzocrea et al., "Effects of Glycogen Synthase Kinase-3β Inhibition on the Decelopement of Cerulein-Induced acute Pancreatitis in Mice", Crit. Care Med, 2007, vol. 35, vol. 12, pp. 2811-2821.

Cuzzocrea et al., "Glycogen Synthase Kinase-3β Inhibition Attenuates the Degree of Arthritis Caused by Type II Collagen in the Mouse", Elsevier, Critical Immunology, 2006, pp. 1-11.

Cuzzocrea et al., "Glycogen Synthase Kinase-3β Inhibition Attenuates the Development of Ischaemia/Reperfusion Injury of the Gut", Intensive Care Med., 2007, pp. 1-14.

Cuzzocrea et al., "Glycogen Synthase Kinase-3β Inhibition Attenuates the Development of Bleomycin-Induces Lung Injury", International Journal of Immunopathology and Pharmacology, 2007, vol. 20, No. 3, pp. 619-630.

Cuzzocrea et al., "Inhibition of Glycogen Synthase Kinase-3β Attenuates the Development of Carrageenan-Induced Lung Injury in Mice", British Journal of Pharmacology, 2006, pp. 1-16.

Dugo et al., "Insulin Reduces the Multiple Organ Injury and Dysfunction Caused by Coadministration of Lipolysaccharide and Peptidoglycan Independently of Blood Glucose: Role of Glycogen Synthase Kinase-3β Inhibition", Crit Care Med, 2006, vol. 34, No. 5, pp. 1-8.

Dugo et al., "Glycogen Synthase Kinase-3β as a Target for Therapy of Shock and Inflammation", Shock, 2007, vol. 27, No. 2, pp. 113-123.

Farago et al., "Kinase-Inactive Glycogen Syntahse Kinase-3β Promotes Wnt Signaling and Mammary Tumorigenesis", Cancer Res., 2005, vol. 65, No. 13, pp. 5792-5801.

Ghosh et al., Activation of p53-Dependent Apoptosis by Acute Ablation of Glycogen Synthase Kinase-3β in Colorectal Cancer Cells:, CLin Cancer Res, 2005, vol. 11, No. 12, pp. 4580-4588.

Guzman et al., "Rapid and Selective Death of Leukemia Stem and Progenitor Cells induced by the Compound 4-benzyl, 2-methyl, 1,2,4-thiadiazolidine, 3,5 dione (TDZD-8)", Blood, 2007, vol. 110, No. 13, pp. 4436-4444.

Jordan, Craig T., "The Leukemic Stem Cell", Best Practice & Research Clinical Haematology, 2007, vol. 20, No. 1, pp. 13-18.

Sun et al., "Lithium Suppresses Cell Proliferation by Interrupting E2F-DNA Interaction and Subsequently Reducing S-Phase Gene Expression in Prostate Cancer", The Prostate, 2007, vol. 67, pp. 976-988.

Whittle et al., Reduction of Experimental Colitis in the Rat by Inhibitors of Glycogen Synthase Kinase-3β, British Journal of Pharmacology, 2005, pp. 1-8.

Andricopulo et al., "Structure-Activity Relationships for the Design of Small-Molecule Inhibitors", Mim-Reviews in Medicinal Chemistry, 2005, vol. 5, 585-593.

Aoukaty et al., "Role for Glycogen Synthase Kinase-3 in NK Cell Cytotoxicity and X-Linked Lymphoproliferative Disease", The Journal of Immunology, 2005, pp. 4551-4558.

Barry et al., "Regulation of glycogen synthase kinase 3 in human platelets: a possible role in platelet function?", FEBS Letters, 2003, vol. 553, pp. 173-178.

Caricasole et al., "Induction of Dickkopf-1, a Negative Modulator of the Wnt Pathway, Is Associated with Neuronal Degeneration in Alzheimer's Brain", The Journal of Neuroscience, 2004, vol. 24, No. 26, pp. 6027-6021.

Chen et al., "Glycogen synthase kinase 3β (GSK3β) mediates 6-hydroxydopamine-induced neuronal death", The FASEB Journal express article 10.1096/fj.04-1551fje—published online May 7, 2004.

Chin et al., "Inhibition of GSK3β is a common event in neuroprotection by different survival factors", Molecular Brain Research, 2005, vol. 137, pp. 193-201.

Collino et al., "Treatment with the Glycogen Synthase Kinase-3β Inhibitor, TDZD-8, affects transient cerebral ischemia/reperfusion injury in the rat hippocampus", Shock Society, 2008, pp. 1-10.

Cuzzocrea et al., "Glycogen synthase kinase-3β inhibition attenuates the degree of arthritis caused by type II collagen in the mouse", Clinical Immunology, 2006, pp. 1-11.

Cuzzocrea et al., "Glycogen synthase kinase-3β inhibition reduces the development of nonseptic shock induced by zymosan in mice", Shock Society, 2006, pp. 1-13.

Cuzzocrea et al., "Glycogen synthase kinase-3β inhibition reduces secondary damage in experimental spinal cord trauma", JPET Fast Forward, published on Apr. 6, 2006 as DOI:10.1124/jpet.102863, pp. 1-46.

Cuzzocrea et al., "Inhibition of glycogen synthase kinase-3β attenuates the development of carrageenan-induced lung injury in mice", British Journal of Pharmacology, 2006, pp. 1-16.

Ding et al., "Degradation of Mcl-1 by β-TrCP Mediates Glycogen Synthase Kinase 3-Induced Tumor Suppression and Chemosensitization", Molecular and Cellular Biology, 2007, pp. 4006-4017.

Dugo et al., "Glycogen synthase kinase-3β inhibitors protection against the organ injury and dysfunction caused by hemorrhage and resuscitation", Shock, 2006, vol. 25, No. 5, pp. 485-491.

Dugo et al., GSK-3β inhibitors attenuate the organ injury/dysfunction caused by endotoxemia in the rat, Crit. Care Med., 2005, vol. 33, No. 9, pp. 1903-1912.

Engel et al., "Animal models with modified expression of GSK-3 for the study of its physiology and of its implications in human pathologies", Glycogen Synthase Kinase 3 (GSK-3) and its inhibitors, John Wiley & Sons, Inc., 2006, pp. 203-219.

Engle et al., "Cooexpression of FTDP-17 tau and GSK-3 β in transgenic mice induce tau polymerization and neurodegeneration", Neurobiology of Aging, 2005, p. 1-11.

Engle et al., "Full Reversal of Alzheimer's Disease-Like Phenotype in a Mouse Model with Conditional Overexpression of Glycogen Synthase Kinase-3", The Journal of Neuroscience, 2006, pp. 5083-5090.

Esposito et al., "The marijuana component cannabidiol inhibits β-amyloid-induced tau protein hyperphosphorylation through Wnt/β-catenin pathway rescue in PC12 cells", J. Nol. Med. 2006, vol. 84, pp. 253-258.

Eto et al., "Glycogen Synthase Kinase-3 Mediates Endothelial Cell Activation by Tumor Necrosis Factor-α", American Heart Association, Inc., 2005, pp. 1316-1322.

Fang et al., "Protein Breakdown in Muscle from Burned Rats Is Blocked by Insulin-Like Growth Factor I and Glycogen Synthase Kinase-3 β Inhibitors", Endrocrinology, 2005, vol. 146, No. 7, pp. 3141-3149.

Farago et al., "Kinase-Inactive Glycogen Synthase Kinase 3 β Promotes Wnt Signaling and Mammary Tumorigenesis", Cancer Res., 2005, vol. 65, No. 13, pp. 5792-5801.

Fink, Mitchell P., "What do insulin, estrogen, valproic acid, and TDZD-8 have in common", Crit. Care Med., 2005, vol. 33, No. 9, pp. 2115-2117.

Ghosh et al., "Activation of p53-Dependent Apoptosis by Acute Ablation of Glycogen Synthase Kinase-3 β in Colorectal Cancer Cells", Clin. Cancer Res., 2005, vol. 11, No. 12, pp. 4580-4588.

Goodenough et al., "Inactivation of glycogen synthase kinase-3 β protects against kainic acid-induced neurotoxicity in vivo", Brain Research, 2004, pp. 116-125.

Hernandez et al., "Spatial learning deficit in transgenic mice that conditionally over-express GSK-3 β in the brain but do not form tau filaments", Journal of Neurochemistry, 2002, vol. 83, pp. 1529-1533.

Iuvone et al., "The spice sage and its active ingredient rosmarinic acid protect PC12 cells form amyloid- β peptide-induced neurotoxicity", American Society for Pharmacology and Experimental Therapeutics, 2006, pp. 1-33.

Kumar et al., "Application of graph theory: prediction of glycogen synthase kinase-3 β inhibitory activity of thiadiazolidinomes as potential drugs for the treatment of Alzheimer's disease", European Journal of Pharmaceutical Sciences, 2005, vol. 24, pp. 213-218.

Li et al., "Insulin-like growth factor-I inhibits dexamethasone-induced proteolysis in cultured L6 myotubes through P13K/Akt/GSK-3 β and P13K/Akt/mTOR-dependent mechanisms", The International Journal of Biochemistry and Cell Biology, 2005, pp. 1-10.

Meijer et al., "Pharmacological inhibitors of glycogen synthase kinase 3", TRENDS in Pharmacological Sciences, 2004, vol. 25, No. 9, pp. 471-480.

Mühl et al., "Controlling the cytokine storm by insulin: Glycogen synthase kinase-3 as a target in systemic inflammation", Crit. Care Med., 2006, vol. 34, No. 5, pp. 1567-1569.

Ougolkov et al., "Inhibition of glycogen synthase kinase-3 activity leads to epigenetic silencing of nuclear factor $_\kappa$B target genes and induction of apoptosis in chronic lymphocytic leukemia B cells", Blood, 2007, vol. 110, No. 2, pp. 735-742.

Uchida et al., "Semaphorin3A signaling is mediated via sequential Cdk5 and GSK3 β phosporylation of CPMP2: implication of common phosphorylating mechanism underlying axon guidance and Alzheimer's disease", Genes to Cells, 2005, vol. 10, pp. 165-179.

Whittle et al., "Reduction of experimental colitis in the rat by inhibitors of glycogen synthase kinase-3 β", British Journal of Pharmacology, 2006, vol. 147, pp. 575-582.

Zhang et al., "Inhibitory Phosphorylation of Glycogen Synthase Kinase-3 (GSK-3) in Response to Lithium", The Journal of Biological Chemistry, 2003, vol. 278, No. 35, pp. 33067-33077.

NeuroPharma Press Release: "Neuropharma and JSK Research to co-develop transgenic mouse models", 2007, pp. 1-3.

STN Registry No. 89570-37-6, 1984.

Dugo et al., "Insulin reduces the multiple organ injury and dysfunction caused by coadministration of lipopolysaccharide and peptidoglycan independently of blood glucose: Role of glycogen synthase kinase-3β inhibition", Crit. Care Med., 2006, vol. 24, No. 5, pp. 1-.

Evenson et al., "GSK-3 β inhibitors reduce protein degradation in muscles from septic rats and in dexamethasone-treated myotubes", The International Journal of Biochemistry and Cell Biology, 2205, pp. 1-13, 2005.

Jordan, Craig T., "The leukemic stem cell", Best Practice & Research Clinical Haematology, vol. 20, No. 1, pp. 13-18, 2007.

Lucas et al; "Decreased nuclear β-catenin, tau hyperphosphorylation and neurodegeneration in GSK-3 β conditional transgenic mice", The EMBO Journal, vol. 20, No. 1, pp. 27-39, 2001.

ENZYME INHIBITORS

CROSS-REFERENCE TO RELATED APPLICATIONS

This application is a divisional of U.S. application Ser. No.: 10/917,175, filed on Aug. 12, 2004, now U.S. Pat. No. 7,666,885 which is a divisional of U.S. application Ser. No.: 10/290,569 filed on Nov. 8, 2002, now U.S. Pat. No. 6,872,737 which is a continuation-in-part of International Application No.: PCT/GB01/02100, filed on May 11, 2001, which claims the benefit of Spanish Application No.: ES 200001185, filed on May 11, 2000, and Great Britain Application No.: GB 0030284.4, filed on Dec. 12, 2000. The entire contents of each of these prior applications is incorporated herein by reference.

FIELD OF THE INVENTION

The present invention relates to enzyme inhibitors, and more particularly to heterocyclic inhibitors of glycogen synthase kinase 3β, GSK-3.

BACKGROUND OF THE INVENTION

Alzheimer's disease (AD) is a neurodegenerative process characterised by cognitive disorders associated with a progressive deterioration of the cholinergic function, and neuropathological lesions as senile plaques, formed by the fibrillary β-amyloid, and neurofibrillary tangles, bundles of paired helical filaments.

Generally speaking, AD is restricted to groups aged 60 years or more and is the most common cause of dementia in the elderly population. Today, AD affects 23 million people worldwide. As longevity increases, it is estimated that by the year 2050 the number of cases of AD will more than triplicate [Amaduci, L.; Fratiglioni, L. "Epidemiology of AD: Impact on the treatment", in *Alzheimer Disease: Therapeutic Strategies*, E. Giacobini and R. Becker, Eds., Birhäuser, EEUU, 1994, pp. 8].

Two major histological lesions are observed in AD brains associated with the neuronal loss: neurofibrillary tangles and senile plaques at the intracellular and extracellular level respectively ["Alzheimer Disease: From molecular biology to therapy", E. Giacobini and R. Becker, Eds., Birhäuser, EEUU, 1996].

Neurofibrillary tangles are structures formed by paired helical filaments (PHFs). They are comprised mainly of the microtubule-associated protein (MAP) tau in an abnormally hyperphosphorylated state [Grundke-Iqbal, I.; Iqbal, K.; Tung, Y. C.; Quinlan, M.; Wisniewski, H. M.; Binder, L. I., "Abnormal phosphorylation of the microtubule-associated protein tau in Alzheimer cytoskeletal pathology", *Proc. Natl. Acad. Sci. USA*, 1986, 83, 4913-4917; Grundke-Iqbal, I.; Iqbal, K.; Quinlan, M.; Tung, Y. C.; Zaidi, M. S.; Wisniewski, H. M., "Microtubule-associated protein tau. A component of the Alzheimer paired helical filaments", *J. Biol. Chem.*, 1986, 261, 6084-6089; Greenberg, S. G.; Davies, P.; Schein, J. D.; Binder, L. I., "Hydrofluoric acid-treated tau PHF proteins display the same biochemical properties as normal tau.", *J. Biol. Chem.*, 1992, 267, 564-569]. Such aberrant phosphorylation of tau, determined by the effects of different protein kinases and phosphatases, appears to compromise on its ability to bind to and stabilise microtubules and this may contributes to AD pathology [Moreno, F. J.; Medina, M.; Perez, M.; Montejo de Garcini, E.; Avila, J., "Glycogen sintase kinase 3 phosphorylation of different residues in the presence of different factors: Analysis on tau protein", *FEBS Lett.*, 1995, 372, 65-68]. Thus, the blockade of this hyperphosphorylation step may be a prime target at which to interrupt the pathogenic cascade. The selective inhibitors of tau kinases might be new effective drugs for the treatment of AD.

The search for tau kinases inhibitors is a field of a great interest. Tau can be phosphorylated by several proline-directed protein kinases (PDKs) and non-PDKs. However, in AD the exact role of any of these kinases in the abnormal hyperphosphorylation of tau is not yet understood and to date, the activity of these kinases has not been found to be upregulated. It is no doubt that glycogen synthase kinase 3β (GSK-3β) is an in vivo tau kinase in the brain [Lovestone, S.; Hartley, C. L.; Pearce, J.; Anderton, B. H., "Phosphorylation of tau by glycogen synthase-3 in intact mammalian cells: the effects on the organization and stability of microtubules", *Neuroscience*, 1996, 73, 1145-1157; Wagner, U.; Utton, M.; Gallo, J. M.; Miller, C. C., "Cellular phosphorylation of tau by GSK-3β influences tau binding to microtubules and microtubule organisation", *J. Cell. Sci.*, 1996, 109, 1537-1543; Ledesma, M.; Moreno, F. J.; Perez, M. M.; Avila, J., "Binding of apolipoprotein E3 to tau protein: effects on tau glycation, tau phosphorylation and tau-microtubule binding, in vitro", *Alzheimer Res.*, 1996, 2, 85-88]. These findings open the gate to the use of GSK-3β inhibitors as therapeutical agents in the treatment of AD. At the moment few compounds are known with this enzymatic inhibitory property.

Lithium behaves as a specific inhibitor of the GSK-3 family of protein kinases in vitro and in intact cells Muñoz-Montaño, J. R.; Moreno, F. J.; Avila, J.; Diaz-Nido, J., "Lithium inhibits Alzheimer's disease-like tau protein phosphorylation in neurons", *FEBS Lett.*, 1997, 411, 183-188].

Finally, it is observed that insulin inactivates GSK-3 and it is shown that the non-dependent insulin diabetes mellitus is developed with the activation of this enzyme. So that, GSK-3 inhibitors would be a new therapy for the non-dependent insulin diabetes mellitus.

In our work team we have recently discovered a new family of small synthetic heterocyclic molecules with GSK-3β inhibitory properties at micromolar level.

DESCRIPTION OF THE INVENTION

The invention is directed to the compounds represented by the general formula I:

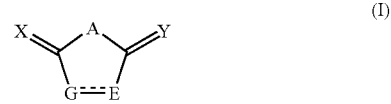

(I)

where:
A is —C(R$^1$)$_2$—, —O— or —NR$^1$—;
E is —NR$^1$— or —CR$^1$R$^2$— and the substituent R$^2$ is absent if - - - is a second bond between E and G;
G is —S—, —NR$^1$— or —CR$^1$R$^2$— and the substituent R$^2$ is absent if - - - is a second bond between E and G;
- - - may be a second bond between E and G where the nature of E and G permits and E with G optionally then forms a fused aryl group;
R$^1$ and R$^2$ are independently selected from hydrogen, alkyl, cycloalkyl, haloalkyl, aryl, —(Z)$_n$-aryl, heteroaryl, —OR$^3$, —C(O)R$^3$, —C(O)OR$^3$, —(Z)$_n$-C(O)OR$^3$ and —S(O)$_t$— or as indicated R$^2$ can be such that E with G then form a fused aryl group;

Z is independently selected from —C($R^3$)($R^4$)—, —C(O)—, —O—, —C(=N$R^3$)—, —S(O)$_t$—, N($R^3$)—;

n is zero, one or two;

t is zero, one or two;

$R^3$ and $R^4$ are independently selected from hydrogen, alkyl, aryl and heterocyclic; and X and Y are independently selected from =O, =S, =N($R^3$) and =C($R^1$)($R^2$).

DETAILED DESCRIPTION OF THE INVENTION

As used in this specification and appended claims, unless specified to the contrary, the following terms have the meaning indicated:

"Alkyl" refers to a straight or branched hydrocarbon chain radical consisting of carbon and hydrogen atoms, containing no saturation, having one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents independently selected from the group consisting of a halo, hydroxy, alkoxy, carboxy, cyano, carbonyl, acyl, alkoxycarbonyl, amino, nitro, mercapto and alkylthio.

"Alkoxy" refers to a radical of the formula —O$R_a$ where $R_a$ is an alkyl radical as defined above, e.g., methoxy, ethoxy, propoxy, etc.

"Alkoxycarbonyl" refers to a radical of the formula —C(O)O$R_a$ where $R_a$ is an alkyl radical as defined above, e.g., methoxycarbonyl, ethoxycarbonyl, propoxycarbonyl, etc.

"Alkylthio" refers to a radical of the formula —S$R_a$ where $R_a$ is an alkyl radical as defined above, e.g., methylthio, ethylthio, propylthio, etc.

"Amino" refers to a radical of the formula —$NH_2$.

"Aryl" refers to a phenyl or naphthyl radical, preferably a phenyl radical. The aryl radical may be optionally substituted by one or more substituents selected from the group consisting of hydroxy, mercapto, halo, alkyl, phenyl, alkoxy, haloalkyl, nitro, cyano, dialkylamino, aminoalkyl, acyl and alkoxycarbonyl, as defined herein.

"Aralkyl" refers to an aryl group linked to an alkyl group. Preferred examples include benzyl and phenethyl.

"Acyl" refers to a radical of the formula —C(O)—$R_c$ and —C(O)—$R_d$ where $R_c$ is an alkyl radical as defined above and $R_d$ is an aryl radical as defined above, e.g., acetyl, propionyl, benzoyl, and the like.

"Aroylalkyl" refers to an alkyl group substituted with —C(O)—$R_d$. Preferred examples include benzoylmethyl.

"Carboxy" refers to a radical of the formula —C(O)OH.

"Cyano" refers to a radical of the formula —CN

"Cycloalkyl" refers to a stable 3- to 10-membered monocyclic or bicyclic radical which is saturated or partially saturated, and which consist solely of carbon and hydrogen atoms. Unless otherwise stated specifically in the specification, the term "cycloalkyl" is meant to include cycloalkyl radicals which are optionally substituted by one or more substituents independently selected from the group consisting of alkyl, halo, hydroxy, amino, cyano, nitro, alkoxy, carboxy and alkoxycarbonyl.

"Fused aryl" refers to an aryl group, especially a phenyl or heteroaryl group, fused to the five-membered ring.

"Halo" refers to bromo, chloro, iodo or fluoro.

"Haloalkyl" refers to an alkyl radical, as defined above, that is substituted by one or more halo radicals, as defined above, e.g., trifluoromethyl, trichloromethyl, 2,2,2-trifluoroethyl, 1-fluoromethyl-2-fluoroethyl, and the like.

"Heterocycle" refers to a heterocyclyl radical. The heterocycle refers to a stable 3- to 15-membered ring which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran. The hetrocycle may be optionally substituted by $R^3$ and $R^4$ as defined above in the summary of the invention.

"Heteroaryl" refers to an aromatic heterocycle

"Mercapto" refers to a radical of the formula —SH

"Nitro" refers to a radical of the formula —$NO_2$

The invention is in particular directed to the enzymatic activity against kinases of the compounds of the general formula I.

A is preferably selected from —C($R^1$)$_2$— and —N$R^1$—.

Preferably $R^1$ is selected from hydrogen, alkyl, cycloalkyl, aryl (optionally substituted with a group selected from alkyl, halo and alkoxy), —C($R^3$)($R^4$)-aryl (the aryl part being optionally substituted with a group selected from alkyl, halo and alkoxy), —O$R^3$, —C(O)O$R^3$ and —C($R^3$)($R^4$)—C(O)O$R^3$, and $R^3$ and $R^4$ are independently selected from hydrogen and alkyl.

The subscript n is preferably zero or one, and n will be chosen having regard to the known chemistry of possible groupings.

X and Y are preferably oxygen or sulphur, at least one of X and Y is preferably oxygen.

A particularly preferred class of compounds is of the formula (II).

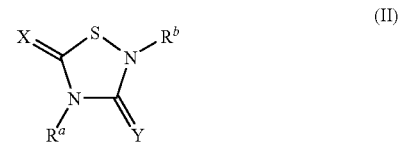

(II)

where $R^a$ and $R^b$ are independently selected from hydrogen, alkyl, cycloalkyl, haloalkyl, aryl, —(Z)$_n$-aryl, heteroaryl, —O$R^3$, —C(O)$R^3$, —C(O)O$R^3$, —(Z)$_n$—C(O)O$R^3$ and —S(O)$_t$—, and Z, n, t, $R^3$, $R^4$, X and Y are as defined above.

In the formula (II), X and Y are preferably selected from oxygen, sulphur, and —NR— where $R^3$ is heterocyclic, especially a 6-membered heterocycle which has one heteroatom which is nitrogen, being optionally aromatic and optionally oxidised or quaternised. More preferably, both X and Y are both oxygen.

Preferably. $R^a$ and $R^b$ are independently selected from hydrogen, alkyl, cycloalkyl, aryl (optionally substituted with a group selected from alkyl, halo and alkoxy), —C($R^3$)($R^4$)-aryl (the aryl part being optionally substituted with a group selected from alkyl, halo and alkoxy), —OR³, —C(O)OR³ and —C(R³)(R⁴)—C(O)OR³, and R³ and R⁴ are independently selected from hydrogen, alkyl and heterocyclic.

More preferably $R^a$ and $R^b$ are independently selected from alkyl, aryl (optionally substituted with a group selected from alkyl, halo and alkoxy), —CH₂-aryl (the aryl part being optionally substituted with a group selected from alkyl, halo and alkoxy), and —CH₂—C(O)OR³ where R³ is hydrogen or alkyl.

Still more preferably, $R^a$ and $R^b$ are independently selected from methyl, ethyl, propyl, benzyl, phenyl (optionally substituted with a group selected from methyl, fluoro, chloro, bromo and methoxy) and —CH₂—C(O)O-ethyl.

The most preferred compounds of formula (II) are listed in Table 1 below.

TABLE 1

| $R^a$ | $R^b$ | X | Y |
|---|---|---|---|
| CH₂Ph | Me | O | O |
| Et | Me | O | O |
| Ph | Me | O | O |
| CH₂CO₂Et | Me | O | O |
| 4-OMePh | Me | O | O |
| 4-MePh | Me | O | O |
| 4-BrPh | Me | O | O |
| 4-FPh | Me | O | O |
| 4-ClPh | Me | O | O |
| CH₂Ph | CH₂Ph | O | S |
| Ph | Ph | O | S |

Another preferred class of compounds of the invention are those compounds of formula (III):

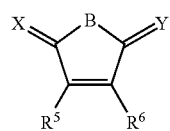

(III)

wherein:
B is —NR⁷— or C(R⁷)(R⁸)— (wherein R⁷ and R⁸ are independently selected from hydrogen, alkyl, aryl, —CH₂—W-aryl, and —W—CO₂H, and W is a single bond, CH₂ or CO);
R⁵ and R⁶ are independently selected from hydrogen, alkyl, aryl and —CH₂-aryl; and
X and Y are independently selected from =O and =S.

In the formula (III), B is preferably —NR—, wherein R⁷ is selected from hydrogen, alkyl and —CH₂-aryl, especially hydrogen, methyl or benzyl.

R⁵ and R⁶ are preferably hydrogen.

X and Y are preferably oxygen.

The most preferred compounds of formula (III) are listed in Table 2 below.

TABLE 2

| B | X | Y | R⁵ | R⁶ |
|---|---|---|---|---|
| NH | O | O | H | H |
| N—CH₂Ph | O | O | H | H |
| NMe | O | O | H | H |
| CH₂ | O | O | H | H |

Examples of further classes of compounds of formula I include those where:

a) A is —CH₂—; E is —CR¹R²—, preferably —CH₂—; G is —CR¹R²—, preferably —CH₂—;

b) A is —CH₂—; E is —CR¹—, preferably —CH—; G is —CR¹—, preferably —CH—; and - - - - is a second bond between G and E;

c) A is —O—; E is —CR¹—, preferably —CH—; G is —CR¹—, preferably —CH—; and - - - - is a second bond between G and E;

d) A is —NR¹—, where R¹ is preferably hydrogen, alkyl or aralkyl; E is —CR¹—, preferably —CH—; G is —CR¹—, preferably —CH—; and - - - - is a second bond between G and E;

e) A is —NR¹—, where R¹ is preferably hydrogen or aralkyl; E is —CR¹R²—, preferably —CH₂—; G is —CR¹R²—, preferably —CH₂—;

f) A is —NR¹—, where R¹ is preferably hydrogen or aralkyl; E is —CR¹—; G is —CR¹—; - - - - is a second bond between E and G; and E with G form a fused aryl group, preferably a phenyl group;

g) A is —NR¹—, where R¹ is preferably hydrogen, alkyl, carboxyalkyl, aroylalkyl or aralkyl; E is —S; G is —C(R¹)₂—, preferably —CH₂—;

h) A is —NR¹—, where R¹ is preferably aryl; E is —NR¹—, where R¹ is preferably hydrogen or alkyl; G is —NR¹—, where R¹ is preferably hydrogen or alkyl.

In these classes of compounds, X and Y are preferably both O, though for class (g) X can be O and Y can be S. When E with G form a fused phenyl group, the resultant compounds are phthalimido derivatives.

Synthesis of the Compounds of the Invention

The compounds of the invention can be synthesised by available procedures.

For preferred compounds of formula (II) a general procedure is available [Martinez, A.; Castro, A.; Cardelús, I.; Llenas, J.; Palacios, J. M. *Bioorg. Med. Chem.*, 1997, 5, 1275-1283].

Concretely, the compounds of general formula (II) and collected in Table I, were prepared following the synthetic procedure depicted in scheme 1, and using the reactivity of N-alkyl-S—[N'-chlorocarbamoyl)amino]isothiocarbamoyl chlorides with different alkyl isocyanates. The isothiocyanates chlorination is performed by addition of an equimolecular quantity of chlorine over an hexane solution of the mentioned isothiocyanate at −15° C. The reaction of the iminochloroalkylsulfenyl chloride formed with alkyl or aryl isocyanate under inert atmosphere and subsequent hydrolysis, yielded the thiadiazolidinediones described in table I.

Scheme 1

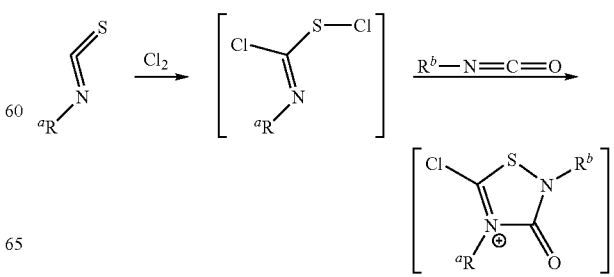

-continued

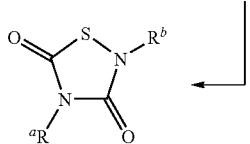

The typical compounds of this invention selectively inhibit GSK-3β without inhibition of others protein kinases such as PKA, PKC, CK-2 and CdK2, which could eliminate the widespread effects. GSK-3β is involved in the aetiopathogenesis of AD and it is responsible for the abnormal hyperphosphorylation of the tau protein. The selective inhibitors here disclosed can be useful therapeutical agents for the treatment of neurodegeneratives diseases associated to the pathology of tau protein, specially for AD which forms part of this invention. The inhibitory action of these compounds against GSK-3β leads for the design of drugs able to stop the formation of the neurofibrilar tangles, one of the hallmark present in this neurodegenerative process.

These compounds can be useful for the treatment of other pathologies in which the GSK-3β is involved, such as non-insulin-dependent diabetes mellitus.

Additionally, these compounds can be useful for the treatment of hyperproliferative diseases such as displasias and metaplasias of different tissues, psoriasis, artherioschlerosis, resthenosis and cancer, due to their inhibition of cellular cycle which forms part of this invention.

Accordingly, the present invention further provides pharmaceutical compositions comprising a compound of this invention together with a pharmaceutically acceptable carrier or diluent. Appropriate dosage forms and dosing rates can be devised and adopted in accordance with conventional practice.

EXAMPLES

Example 1

Enzymatic Inhibition of the Compounds of the Invention

GSK-3β inhibition: The GSK-3 activity was determined by incubation of a mixture of GSK-3 enzyme (Sigma), a phosphate source and a GSK-3 substrate in the presence and in the absence of the corresponding test compound, and by measuring the GSK-3 activity of this mixture.

Concretely, the GSK-3 activity is determined by incubating the enzyme at 37° C. during 20 minutes in a final volume of 12 μl of buffer (50 mM tris, pH=7.5, 1 mM EDTA, 1 mM EGTA, 1 mM DTT, 10 mM $Cl_2Mg$) supplemented with 15 μM (final concentration) of the synthetic peptide GS 1 [Woodgett, J. R. "Use of peptides for affinity purification of protein-serine kinases", *Anal. Biochem.*, 1989, 180, 237-241] as substrate, 15 μM of ATP, 0.2 μ$C_i$ of [γ-$^{32}$P]ATP and different concentrations of the test compound. The reaction is quenched by addition of an aliquot of the reaction mixture in phosphocelullose p81 papers. These papers are washed three times with phosphoric acid 1% and the radioactivity incorporated to the GS 1 peptide is measured in a liquid scintillation counter.

Compounds showed in table 1 are representative of the GSK-3 inhibitory activity object of this invention. The $IC_{50}$ (concentration at which a 50% of enzyme inhibition is shown) values are gathered in Table 3 below. The synthesis of the compounds listed in Table 3 is described below.

TABLE 3

(II)

| Compound No. | $R^a$ | $R^b$ | X | Y | $IC_{50}$ (μM) |
|---|---|---|---|---|---|
| 1 | $CH_2Ph$ | Me | O | O | 1 |
| 2 | Et | Me | O | O | 5 |
| 3 | Et | nPr | O | O | 10 |
| 4 | Et | cyclohexyl | O | O | 10 |
| 5 | Ph | Me | O | O | 2 |
| 6 | $CH_2CO_2Et$ | Me | O | O | 5 |
| 7 | 4-OMePh | Me | O | O | 5 |
| 8 | $CH_2Ph$ | Et | O | O | 7 |
| 9 | Et | iPr | O | O | 35 |
| 10 | $CH_2Ph$ | Et | O | S | 6 |
| 11 | $CH_2Ph$ | $CH_2Ph$ | O | S | 10 |
| 12 | Ph | Ph | O | S | 20 |
| 13 | Et | Et | O | S | 20 |
| 14 | Cyclohexyl | Me | O | O | >100 |
| 15 | 4-MePh | Me | O | O | 5 |
| 16 | 4-BrPh | Me | O | O | 3 |
| 17 | 4-FPh | Me | O | O | 4 |
| 18 | 4-ClPh | Me | O | O | 4 |
| 19 | Et | Me | 2-pyridylimino | O | >100 |
| 20 | Et | Et | 2-pyridylimino | O | >100 |
| 21 | Et | H | 2-pyridylimino | O | >100 |
| 22 | Me | Me | 2-pyridylimino | O | >100 |
| 23 | Et | Me | 3-pyridylimino N-oxide | O | >100 |
| 24 | Et | Me | 1-methylpyridin-3-yl imino | O | >100 |
| 25 | Et | Me | 1-methylpiperidin-3-yl imino | O | >100 |
| 26 | Et | Me | 2-pyridylimino | S | 10 |

Method for the Synthesis of the Compounds Depicted in Table 3

General Method for the Synthesis of 1,2,4-thiadiazolidin-3,5-diones (Compounds 1-18)

Chlorine generated by the addition of 35% HCl to $KMnO_4$) was bubbled slowly through a solution of aryl or alkyl isothiocyanate in dry hexane (25 ml), under a nitrogen atmosphere, at $-15°$ C. to $-10°$ C. The temperature of the reaction mixture was carefully controlled during the addition step. At this point, the N-aryl or N-alkyl-S-chloroisothiocarbamoyl chloride (see Scheme 1 above) was formed. Afterwards, alkyl isocyanate was added, and the mixture was stirred at room temperature for between 8 and 10 h. After this time, the resulting product was purified by suction filtration and recrystallization or silica gel column chromatography using the appropriate eluant. Sometimes, the 5-oxo-1,2,4-thiadiazolidine-3-thione was isolated as a by-product.

Specific Methods and Data for the Compounds Listed in Table 3

4-Benzyl-2-methyl-1,2,4-thiadiazolidine-3,5-dione (Compound 1) and 2,4-Dibenzyl-5-oxo-thiadiazolidine-3-thione (Compound 11)

Reagents: Benzyl iso-thiocyanate (0.86 ml, 6.5 mmol), 35% HCl (3.1 ml), $KMnO_4$ (0.5 g), methyl isocyanate (0.38 ml, 6.5 mmol).
Conditions: Room temperature, 8 h.
Isolation (1): filtration of reaction mixture.
Purification: recrystallization from hexane.
Yield: 0.75 g (35%) as white solid; mp 60-61° C.
$^1$H-NMR ($CDCl_3$): 3.2 (s, 3H, $CH_3$); 4.8 (s, 2H, $CH_2$-Bn); 7.31-7.45 (m, 5H, arom.).
$^{13}$C-NMR ($CDCl_3$): 31.4 ($CH_3$); 46.0 ($CH_2$-Bn) 128.2; 128.6; 128.8; 135.1 (C, arom.); 155.2 (3-C=O); 165.6 (5-C=O) Anal. ($C_{10}H_{10}N_2SO_2$) C, H, N, S.
Isolation (11): The filtrate was evaporated.
Purification: silica gel column chromatography using $CH_2Cl_2$/Hexane (1:1).
Yield: 0.08 g (8%) as yellow solid; mp 91-95° C.
$^1$H-NMR ($CDCl_3$): 4.52 (s, 2H, $CH_2$-Bn); 5.10 (s, 2H, $CH_2$-Bn); 7.31-7.52 (m, 10H, arom.).
$^{13}$C-NMR ($CDCl_3$): 50.1 ($CH_2$-Bn); 54.3 ($CH_2$-Bn); 128.1; 128.4; 128.9; 135.4 (C, arom.); 127.1; 127.4; 128.4; 138.6 ('C, arom.); 148.1 (3-C=S); 169.0 (5-C=O) Anal. ($C_{16}H_{14}N_2S_2O$) C, H, N, S.

4-Ethyl-2-methyl-1,2,4-thiadiazolidine-3,5-dione (Compound 2)

Synthesis of this compound is described in Martinez, A.; Alonso, D.; Castro, A.; Arán, J. V.; Cardelus, I.; Baños, J. E.; Badía, A., *Arch. Pharm. Pharm. Med. Chem.*, 1999, 332, 191-194, the contents of which are incorporated herein by reference thereto.

4-Ethyl-2-n-propyl-1,2,4-thiadiazolidine-3,5-dione (Compound 3)

Synthesis of this compound is described in Martinez, A.; Alonso, D.; Castro, A.; Arán, J. V.; Cardelus, I.; Baños, J. E.; Badía, A., *Arch. Pharm. Pharm. Med. Chem.*, 1999, 332, 191-194; the contents of which are incorporated herein by reference thereto.

2-Cyclohexyl-4-ethyl-1,2,4-thiadiazolidine-3,5-dione (Compound 4) and 2,4-diethyl-5-oxo-1,2,4-thiadiazolidine-3,5-dione (Compound 13)

Reagents: Ethyl isothiocyanate (0.56 ml, 6.5 mmol), 35% HCl (3.1 ml), $KMnO_4$ (0.5 g), cyclohexyl isocyanate (0.825 ml, 6.5 mmol).
Conditions: Room Temperature, 10 h.
Purification: silica gel column chromatography using AcOEt/Hexane (1:10).
Yield: The first fraction 0.12 g of compound 4 (2%) as yellow oil.
$^1$H-NMR ($CDCl_3$): 1.20 (t, 3H, $CH_2CH_3$, J=7.1 Hz); 1.31 (t, 3H, $CH_2$'$CH_3$, J=7.2 Hz); 3.33 (c, 2H, '$CH_2CH_3$, J=7.2 Hz); 3.89 (c, 2H, $CH_2CH_3$, J=7.1 Hz). $^{13}$C-NMR ($CDCl_3$): 12.2 ($CH_2CH_3$); 15.7 ($CH_2$'$CH_3$); 42.4 ($CH_2CH_3$); 45.8 ('$CH_2CH_3$); 146.3 (3-C=S); 168.2 (5-C=O). Anal. ($C_6H_{10}N_2OS_2$) C, H, N, S.
The second fraction 0.73 mg of compound 13 as white solid (49%); mp=45-48° C.
$^1$H-NMR ($CDCl_3$): 1.20 (t, 3H, $CH_2CH_3$, J=7.1 Hz); 1.31-1.92 (m, 5H, chex); 3.72 (c, 2H, $CH_2CH_3$, J=7.1 Hz).
$^{13}$C-NMR ($CDCl_3$): 13.0 ($CH_2CH_3$); 39.8 ($CH_2CH_3$); 24.7; 25.1; 31.73; 53.71(C, chex); 152.2 (3-C=O); 166.2 (5-C=O) Anal. ($C_{10}H_{16}N_2O_2S$) C, H, N, S.

4-Phenyl-2-methyl-1,2,4-thiadiazolidin-3,5-dione (Compound 5) and 2,4-diphenyl-5-oxo-thiadiazolidine-3-thione (Compound 12)

Reagents: Phenyl isothiocyanate (0.78 ml, 6.5 mmol), 35% HCl (3.1 ml), $KMnO_4$ (0.5 g), methyl isocyanate (0.38 ml, 6.5 mmol).
Conditions: Room temperature, 8 h.
Isolation (5): filtration of reaction mixture.
Purification: recrystallization from methanol.
Yield: 0.25 g (30%) as white solid; mp 174-179° C.
$^1$H-NMR ($CDCl_3$): 3.21 (s, 3H, $CH_3$); 7.31-7.50 (m, 5H, arom.).
$^{13}$C-NMR ($CDCl_3$): 31.7 ($CH_3$); 127.2; 129.2; 129.4; 132.7 (C, arom.); 152.7 (3-C=O); 165.3 (5-C=O). Anal. ($C_8H_8N_2SO_2$) C, H, N, S.
Isolation (12): The filtrate was evaporated.
Purification: silica gel column chromatography using $CH_2Cl_2$.
Yield: 0.14 g (15%) as yellow solid; mp 105-110° C.
$^1$H-NMR ($CDCl_3$): 6.70-7.01 (m, 5H, arom); 7.12-7.33 (m, 5H, 'arom.).
$^{13}$C-NMR ($CDCl_3$): 127.2; 128.6; 129.4; 132.7 (C, arom.); 128.7; 129.2; 129.7; 146.7 ('C, arom.); 152.4 (3-C=S); 169.3 (5-C=O). Anal. ($C_{14}H_{10}N_2S_2O$) C, H, N, S.
The synthesis of compound 5 by a different synthetic route is described in Slomezynska, U.; Barany, G., *J. Heterocyclic. Chem.*, 1984, 21, 241, the contents of which are incorporated herein by reference thereto.

4-(Ethoxycarbonylmethyl)-2-methyl-1,2,4-thiadiazolidine-3,5-dione (Compound 6)

Reagents: Ethyl isothiocyanatoacetate (0.8 ml, 6.5 mmol), 35% HCl (3.1 ml), $KMnO_4$ (0.5 g), methyl isocyanate (0.38 ml, 6.5 mmol).
Conditions: Room temperature, 8 h.
Isolation: filtration of reaction mixture.
Purification: recrystallization from hexane.
Yield 0.28 g (20%) as white solid; mp 67-69° C.

¹H-NMR (CDCl₃): 1.3 (t, 3H, CH₂CO₂CH₂CH₃, J=7.1 Hz); 3.2 (s, 3H, CH₃); 4.2 (c, 2H, CH₂CO₂CH₂CH₃, J=7.1 Hz); 4.4 (s, 2H, CH₂CO₂CH₂CH₃)

¹³C-NMR (CDCl₃): 14.0 (CH₂CO₂CH₂CH₃); 31.5 (CH₃); 42.7 (CH₂CO₂CH₂CH₃); 62.1 (CH₂CO₂CH₂CH₃); 152.6 (3-C=O); 166.4 (5-C=O); 166.4 (CO₂). Anal. (C₇H₁₀N₂SO₃) C, H, N, S.

4-(4-Methoxyphenyl)-2-methyl-1,2,4-thiadiazolidine-3,5-dione (Compound 7)

Reagents: 4-methoxyphenyl isothiocyanate (0.89 ml, 6.5 mmol), 35% HCl (3.1 ml), KMnO₄ (0.5 g), methyl isocyanate (0.38 ml, 6.5 mmol).
Conditions: Room temperature, 8 h.
Isolation: filtration of reaction mixture.
Purification: recrystallization from CH₂Cl₂/Hexane.
Yield: 0.44 g (30%) as white solid; mp 140-144° C.
¹H-NMR (CDCl₃): 3.31 (s, 3H, CH₃); 3.80 (s, 3 H, p-CH₃O-Ph); 7.02-7.32 (m, 4H, arom.).
¹³C-NMR (CDCl₃): 31.7 (CH₃); 55.5 (p-CH₃O-Ph); 114.7; 125.3; 128.5; 159.9 (C, arom.); 152.9 (3-C=O); 165.5 (5-C=O). Anal. (C₁₀H₁₀N₂SO₃) C, H, N, S.

4-Benzyl-2-ethyl-1,2,4-thiadiazolidine-3,5-dione (Compound 8)

Reagents: Benzyl isothiocyanate (0.86 ml, 6.5 mmol), 35% HCl (3.1 ml), KMnO₄ (0.5 g), ethyl isocyanate (0.51 ml, 6.5 mmol).
Conditions: Room temperature, 10 h. Purification: silica gel column chromatography using CH₂Cl₂/Hexane (1:1) and CCTLC using CH₂Cl₂.
Yield: 0.39 g (25%) as yellow oil.
¹H-NMR (CDCl₃): 1.22 (t, 3H, CH₂'CH₃, J=7.2 Hz); 3.7 (c, 2H, 'CH₂CH₃, J=7.2 Hz); 4.8 (s, 2H, CH₂-Bn); 7.32-7.44 (m, 5H, arom.)
¹³C-NMR (CDCl₃): 13.7 (CH₂'CH₃); 39.9 ('CH₂CH₃); 45.8 (CH₂-Bn); 128.1; 128.6; 128.8; 135.1 (C, arom.); 152.6 (3-C=O); 165.9 (5-C=O). Anal. (C₁₁H₁₂N₂SO₂) C, H, N, S.

4-Ethyl-2-isopropyl-1,2,4-thiadiazolidin-3,5-dione (Compound 9)

Synthesis of this compound is described in: Martinez, A.; Castro, A.; Cardelús, I.; Llenas, J.; Palacios, J. M., *Bioorg. Med. Chem.*, 1997, 5, 1275-1283, the contents of which are incorporated herein by reference thereto.

4-Benzyl-2-ethyl-5-oxo-1,2,4-thiadiazolidine-3-thione (Compound 10)

Reagents: Benzyl isothiocyanate (0.86 ml, 6.5 mmol), 35% HCl (3.1 ml), KMnO₄ (0.5 g), ethyl isocyanate (0.57 ml, 6.5 mmol).
Conditions: Room temperature, 12 h.
Isolation: solvent evaporation.
Purification: silica gel column chromatography using CH₂Cl₂/Hexane (1:2) first and preparative thin layer chromatography using CH₂Cl₂/Hexane (1:10) after.
Yield: 0.04 g (3%) as yellow oil.
¹H-NMR (CDCl₃): 1.2 (t, 3H, CH₂CH₃, J=7.0 Hz); 4.25 (c, 2H, CH₂CH₃, J=7.0 Hz); 4.5 (s, 2H, CH₂-Bn); 7.11-7.31 (m, 5H, arom.).

¹³C-NMR (CDCl₃): 11.2 (CH₂CH₃); 46.1 (CH₂-Bn); 56.2 (CH₂CH₃); 127.2; 127.3; 128.6; 138.3 (C, arom.); 154.3 (3-C=S); 168.7 (5-C=O). Anal. (C₁₁H₁₂N₂S₂O) C, H, N, S.

4-(4-Methylphenyl)-2-methyl-1,2,4-thiadiazolidine-3,5-dione (Compound 15)

Reagents: 4-Methylphenyl isothiocyanate (0.88 ml, 6.5 mmol), 35% HCl (3.1 ml), KMnO₄ (0.5 g), methyl isocyanate (0.38 ml, 6.5 mmol).
Conditions: Room temperature, 6 h.
Isolation: filtration of reaction mixture.
Purification: recrystallization from CH₂Cl₂/Hexane.
Yield: 0.29 g (21%) as white solid; mp 182-184° C.
¹H-NMR (CDCl₃): 2.4 (s, 3 H, p-CH₃-Ph); 3.25 (s, 3H, CH₃); 7.20-7.34 (m, 4H, arom.).
¹³C-NMR (CDCl₃): 21.1 (p-CH₃-Ph); 31.7 (CH₃); 126.7; 130.0; 130.3; 139.3 (C, arom.); 152.9 (3-C=O); 165.3 (5-C=O). Anal. (C₁₀H₁₀N₂SO₂) C, H, N, S.

4-(4-Bromophenyl)-2-methyl-1,2,4-thiadiazolidine-3,5-dione (Compound 16)

Reagents: 4-Bromophenyl isothiocyanate (1.4 g, 6.5 mmol), 35% HCl (3.1 ml), KMnO₄ (0.5 g), methyl isocyanate (0.38 ml, 6.5 mmol).
Conditions: Room temperature, 9 h.
Isolation: filtration of reaction mixture.
Purification: recrystallization from hexane/CH₂Cl₂.
Yield: 0.32 g (20%) as white solid; mp 182-184° C.
¹H-NMR (CDCl₃): 3.25 (s, 3H, CH₃); 7.25-7.61 (2 d, 4H, arom., J=8.6 Hz).
¹³C-NMR (CDCl₃): 31.6 (CH₃); 123.0; 128.6; 131.6; 132.5 (C, arom.); 153.4 (3-C=O); 165.7 (5-C=O). Anal. (C₉H₇N₂SO₂Br) C, H, N, S.

4-(4-Fluorophenyl)-2-methyl-1,2,4-thiadiazolidine-3,5-dione (Compound 17)

Reagents: 4-Fluorophenyl isothiocyanate (1.1 g, 6.5 mmol), 35% HCl (3.1 ml), KMnO₄ (0.5 g), methyl isocyanate (0.38 ml, 6.5 mmol).
Conditions: Room temperature, 8 h.
Isolation: filtration of reaction mixture.
Purification: recrystallization from ethanol.
Yield: 0.37 g (25%) as white solid; mp 178-180° C.
¹H-NMR (CDCl₃): 3.25 (s, 3H, CH₃); 7.13-7.36 (m, 4H, arom.).
¹³C-NMR (CDCl₃): 31.7 (CH₃); 116.3; 129.1; 160.9; 164.2 (C, arom.); 152.5 (3-C=O); 165.2 (5-C=O). Anal. (C₉H₇N₂SO₂F) C, H, N, S.

4-(4-Chlorophenyl)-2-methyl-1,2,4-thiadiazolidine-3,5-dione (Compound 18)

Reagents: 4-Chlorophenyl isothiocyanate (1.1 g, 6.5 mmol), 35% HCl (3.1 ml), KMnO₄ (0.5 g), methyl isocyanate (0.38 ml, 6.5 mmol).
Conditions: Room temperature, 6 h.
Isolation: filtration of reaction mixture.
Purification: recrystallization from ethanol.
Yield: 0.47 g (30%) as white solid; mp 175-178° C.
¹H-NMR (CDCl₃): 3.25 (s, 3H, CH₃); 7.32-7.44 (2 d, 4H, arom., J=8.9 Hz).
¹³C-NMR (CDCl₃): 31.7 (CH₃); 128.4; 129.6; 131.2; 135.1 (C, arom.); 152.3 (3-C=O); 165.0 (5-C=O). Anal. (C₉H₇N₂SO₂Cl) C, H, N, S.

Synthesis of 5-(2-pyridylimino)-1,2,4-thiadiazolidin-3-ones (Compounds 19-22 and 26)

A general method for the synthesis of these compounds is described in Martinez, A.; Castro, A.; Cardelús, I.; Llenas, J.; Palacios, J. M., *Bioorg. Med. Chem.*, 1997, 5, 1275-1283, the contents of which are incorporated herein by reference thereto.

3-(4-Ethyl-3-oxo-2-methyl-1,2,4-thiadiazolidin-5-ylidine)aminopyridine-1-oxide (Compound 23)

A general method for the synthesis of this compound is described in Martinez, A.; Alonso, D.; Castro, A.; Arán, J. V.; Cardelus, I.; Baños, J. E.; Badía, A., *Arch. Pharm. Pharm. Med. Chem.*, 1999, 332, 191-194, the contents of which are incorporated herein by reference thereto.

3-[5-(4-Ethyl-2-methyl-3-oxo)imino-1,2,4-thiadiazolidyl]-1-methyl-pyridinium iodide (Compound 24)

A general method for the synthesis of this compound is described in Martinez, A.; Alonso, D.; Castro, A.; Gutierrez-Puebla, E.; Baños, J. E.; Badia, A., *Eur. J. Org. Chem.*, 2000, 675-680., the contents of which are incorporated herein by reference thereto.

4-Ethyl-5-[imino-(1-methyl-piperidin-3-yl)]-2-methyl-1,2,4-thiadiazolidin-3-one (Compound 25)

A general method for the synthesis of this compound is described in Martinez, A.; Alonso, D.; Castro, A.; Gutierrez-Puebla, E.; Baños, J. E.; Badia, A., *Eur. J. Org. Chem.*, 2000, 675-680, the contents of which are incorporated herein by reference thereto.

Further compounds of formula (II) have been synthesised and their GSK-3 inhibition tested. These compounds are listed in Table 3a below.

TABLE 3a

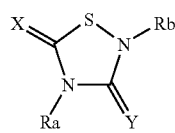

(II)

| Compound No. | $R^a$ | $R^b$ | X | Y | IC$_{50}$ (μM) | Ref. |
|---|---|---|---|---|---|---|
| 27 | Et | Et | O | O | 25 | JMC, JHC |
| 28 | Et | Et | O | S | 20 | JMC |
| 29 | Bn | Bn | O | O | 10 | JMC, JHC |
| 30 | CH$_2$CO$_2$Et | Et | O | O | 10 | below |
| 31 | CH$_2$Ph | COPh | O | O | 3 | below |
| 32 | Ph | Et | O | NH | 65 | JMC |
| 33 | CH$_2$Ph | CH$_2$CO$_2$Et | O | O | 4 | below |
| 34 | 4-CF$_3$Ph | Me | O | O | 6 | JMC |
| 35 | n-Bu | Et | O | O | 70 | JMC |
| 36 | CH$_2$Ph | Et | O | N—OH | 6 | below |
| 37 | 3-BrPh | Me | O | O | 4 | JMC |
| 38 | 2-BrPh | Me | O | O | 6 | JMC |
| 39 | Ph | Et | O | NCONHEt | 75 | JMC |
| 40 | Ph | CO$_2$Et | S | NCO$_2$Et | >10 | JMC |
| 41 | CH$_2$CH$_2$Ph | Et | O | O | 8 | below |
| 42 | CH$_2$Ph | H | O | O | 50 | below |
| 43 | Ph | Et | O | O | 6 | ACIE |
| 44 | CH$_2$CO$_2$Et | CH$_2$CO$_2$Et | O | O | 4 | below |

TABLE 3a-continued

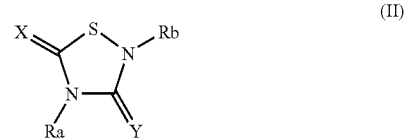

(II)

| Compound No. | $R^a$ | $R^b$ | X | Y | IC$_{50}$ (μM) | Ref. |
|---|---|---|---|---|---|---|
| 45 | CH$_2$CO$_2$Et | Me | O | O | 2 | below |
| 46 | CH$_2$CO$_2$Et | iPr | O | O | 7 | below |
| 47 | CH$_2$CO$_2$Et | Bz | O | O | 4 | below |
| 48 | Naphthyl | Me | O | O | 3 | JMC |
| 49 | 4-NO$_2$-Ph | Et | O | O | 8.5 | below |
| 50 | Ph | Et | O | N—OH | 100 | below |
| 51 | CH$_2$Ph | iPr | O | O | 10 | below |
| 52 | Ph | Ph | O | O | 8 | ACIE |
| 53 | 4-MeOPh | Et | O | O |  | below |
| 54 | 4-MePh | Et | O | O |  | below |
| 55 | 4-BrPh | Et | O | O |  | below |

The synthesis of the known compounds depicted in Table 3a is described in the following publications, the contents of which are incorporated herein by reference thereto:

JMC: Martinez, A; Alonso, M.; Castro, A.; Perez, C.; Moreno, F. J. *J. Med. Chem.* (2002) 2-1299.
JHC: *J. Heterocyclic Chem.* (1984) 21:241.
ACIE: *Angew Chem. Int. Ed.* (1966) 5:672.

The synthesis of the new compounds depicted in Table 3a is described below.

4-(Ethoxycarbonylmethyl)-2-ethyl-1,2,4-thiadiazolidine-3,5-dione (Compound 30)

Reagents: Ethyl isothiocyanatoacetate (0.8 ml, 6.5 mmol), 35% HCl (3.1 ml), KMnO$_4$ (0.5 g), ethyl isocyanate (0.51 ml, 6.5 mmol).
Conditions: Room temperature, 8 h.
Isolation: filtration of reaction mixture.
Purification: recrystallization from hexane.
Yield 0.52 g (34%) as white solid; mp 62-63° C.
$^1$H-NMR (CDCl$_3$): 1.3 (t, 3H, CH$_2$CO$_2$CH$_2$CH$_3$, J=7.1 Hz); 1.3 (t, 3H, CH$_2$CH$_3$, J=7.1 Hz); 3.7 (c, 2H, CH$_2$CH$_3$, J=7.1 Hz); 4.2 (c, 2H, CH$_2$CO$_2$CH$_2$CH$_3$, J=7.1 Hz); 4.4 (s, 2H, CH$_2$CO$_2$CH$_2$CH$_3$).
$^{13}$C-NMR (CDCl$_3$): 13.7 (CH$_2$CH$_3$); 14.0 (CH$_2$CO$_2$CH$_2$CH$_3$); 40.1 (CH$_2$CH$_3$); 42.6 (CH$_2$CO$_2$CH$_2$CH$_3$); 62.1 (CH$_2$CO$_2$CH$_2$CH$_3$); 152.0 (3-C=O); 165.7 (5-C=O); 166.4 (CO$_2$). Anal. (C$_8$H$_{12}$N$_2$SO$_3$) C, H, N, S.

2-Benzoyl-4-benzyl-1,2,4-thiadiazolidine-3,5-dione (Compound 31)

Reagents: Benzyl isothiocyanate (0.86 ml, 6.5 mmol), 35% HCl (3.1 ml), KMnO$_4$ (0.5 g), benzoyl isocyanate (0.81 ml, 6.5 mmol).
Conditions: Room temperature, 9 h.
Isolation: solvent evaporation.
Purification: silica gel column chromatography using AcOEt/Hexane (1:10).
Yield: 0.2 g (10%) as white solid.
$^1$H-NMR (CDCl$_3$): 4.8 (s, 2H, CH$_2$-Ph); 7.3-7.7 (m, 10H, arom.).

¹³C-NMR (CDCl₃): 45.9 (CH₂-Ph); 127.9; 128.5; 128.8; 129.0; 129.2; 132.9; 134.3 (C, arom); 149.0 (3-C=O); 164.7 (COPh); 166.5 (5-C=O). Anal. ($C_{16}H_{12}N_2SO_3$) C, H, N, S.

4-Benzyl-2-(Ethoxycarbonylmethyl)-1,2,4-thiadiazolidine-3,5-dione (Compound 33)

Reagents: Benzyl isothiocyanate (0.86 ml, 6.5 mmol), 35% HCl (3.1 ml), KMnO₄ (0.5 g), Ethyl isocyanatoacetate (0.73 ml, 6.5 mmol).

Conditions: Room temperature, 9 h.

Isolation: solvent evaporation.

Purification: silica gel column chromatography using AcOEt/Hexane (1:6).

Yield: 0.75 g (39%) as colorless oil.

¹H-NMR (CDCl₃): 1.25 (t, 3H, CH₂CO₂CH₂CH₃, J=7.1 Hz); 4.21 (c, 2H, CH₂CO₂CH₂CH₃, J=7.1 Hz); 4.30 (s, 2H, CH₂CO₂CH₂CH₃); 4.8 (s, CH₂-Ph; 7.3-7.5 (m, 5H, arom.).

¹³C-NMR (CDCl₃): 13.7 (CH₂CO₂CH₂CH₃); 45.3 (CH₂CO₂CH₂CH₃); 45.7 (CH₂-Ph); 127.3; 128.3; 128.4; 134.7 (C, arom.); 153.3 (3-C=O); 165.7 (5-C=O); 166.8 (CH₂CO₂CH₂CH₃). Anal. ($C_{13}H_{14}N_2SO_4$) C, H, N, S.

4-Benzyl-2-ethyl-1,2,4-thiadiazolidine-3-one-5-oxime (Compound 36)

Reagents: 5-chloro-4-benzyl-2-ethyl-3-oxo-1,2,4-thiadiazolium chloride (1.24 g, 4.5 mmol), hydroxylamine hydrochloride (0.35 g, 5 mmol), pyridine (0.8 ml, 10 mmol).

Conditions: Room temperature, 12 h.

Isolation: solvent evaporation.

Purification: silica gel column chromatography using AcOEt/Hexane (1:6).

Yield: 0.10 g (9%) as yellow oil.

¹H-NMR (CDCl₃): 1.22 (t, 3H, CH₂CH₃, J=7.1 Hz); 3.60 (c, 2H, CH₂CH₃, J=7.1 Hz); 4.78 (s, 2H, CH₂Ph); 6.57 (s, 1H, N—OH); 7.24-7.40 (m, 5H, arom).

¹³C-NMR (CDCl₃): 13.5 (CH₂CH₃); 40.2 (CH₂CH₃); 46.9 (CH₂Ph); 127.8; 128.4; 128.5; 135.2 (C, arom.); 152.2 (3-C=O); 154.6 (5-C=NOH). Anal. ($C_{11}H_{13}N_3SO_2$) C, H, N, S.

2-Ethyl-4-phenethyl-1,2,4-thiadiazolidine-3,5-dione (Compound 41)

Reagents: phenethyl isothiocyanate (0.97 ml, 6.5 mmol), 35% HCl (3.1 ml), KMnO₄ (0.5 g), ethyl isocyanate (0.51 ml, 6.5 mmol).

Conditions: Room temperature, 10 h.

Isolation: solvent evaporation.

Purification: silica gel column chromatography using AcOEt/Hexane (1:6).

Yield: 0.26 g (16%) as yellow oil.

¹H-NMR (CDCl₃): 1.22 (t, 3H, CH₂CH₃, J=7.1 Hz); 2.95 (m, 2H, CH₂CH₂Ph); 3.63 (c, 2H, CH₂CH₃, J=7.1 Hz); 3.89 (m, 2H, CH₂CH₂Ph); 7.20-7.29 (m, 5H, arom).

¹³C-NMR (CDCl₃): 13.6 (CH₂CH₃); 33.6 (CH₂CH₂Ph); 39.9 (CH₂CH₂Ph); 43.5 (CH₂CH₃); 126.6; 128.5; 128.8; 137.3 (C, arom.); 152.7 (3-C=O); 165.7 (5-C=O) Anal. ($C_{12}H_{14}N_2SO_2$) C, H, N, S.

4-Benzyl-1,2,4-thiadiazolidine-3,5-dione (Compound 42)

Reagents: Benzyl isothiocyanate (0.81 ml, 6.5 mmol), 35% HCl (3.1 ml), KMnO₄ (0.5 g), ethyl isocyanatoformate (0.69 ml, 6.5 mmol).

Conditions: Room temperature, 8 h.

Isolation: Deprotection in situ of the nitrogen with acid conditions.

Purification: preparative centrifugal circular thin layer chromatography (CCTLC) using CH₂Cl₂.

Yield: 0.01 g (1%) as colourless oil.

¹H-NMR (CDCl₃): 4.4 (s, 2H, CH₂Ph); 6.1 (br, NH); 7.1-7.3 (m, 5H, arom.).

¹³C-NMR (CDCl₃): 51.1 (CH₂Ph); 127.1; 128.3; 129.2; 139.6 (C, arom.); 152.1 (3-C=O); 165.6 (5-C=O). Anal. ($C_9H_8N_2SO_2$) C, H, N, S.

4-(Ethoxycarbonylmethyl)-2-(ethoxycarbonylmethyl)-1,2,4-thiadiazolidine-3,5-dione (Compound 44)

Reagents: Ethyl isothiocyanatoacetate (0.8 ml, 6.5 mmol), 35% HCl (3.1 ml), KMnO₄ (0.5 g), ethyl isocyanatoacetate (0.73 ml, 6.5 mmol).

Conditions: Room temperature, 9 h.

Isolation: solvent evaporation.

Purification: silica gel column chromatography using AcOEt/Hexane (1:3).

Yield: 0.90 g (48%) as white solid; mp. 72-74° C.

¹H-NMR (CDCl₃): 1.25 (t, 3H, 'CH₂CO₂CH₂CH₃, J=7.1 Hz); 1.26 (t, 3H, CH₂CO₂CH₂CH₃, J=7.1 Hz); 4.18 (c, 2H, 'CH₂CO₂CH₂CH₃, J=7.1 Hz); 4.20 (c, 2H, CH₂CO₂CH₂CH₃, J=7.1); 4.3 (s, 2H, 'CH₂CO₂CH₂CH₃); 4.4 (s, 2H, CH₂CO₂CH₂CH₃).

¹³C-NMR (CDCl₃): 14.0 ('CH₂CO₂CH₂CH₃); 14.0 (CH₂CO₂CH₂CH₃); 42.7 (CH₂CO₂CH₂CH₃); 45.6 ('CH₂CO₂CH₂CH₃); 62.1 ('CH₂CO₂CH₂CH₃); 62.1 (CH₂CO₂CH₂CH₃); 153.0 (3-C=O); 165.7 (5-C=O); 166.1 (CH₂CO₂CH₂CH₃); 166.8 ('CH₂CO₂CH₂CH₃). Anal. ($C_{10}H_{14}N_2SO_6$) C, H, N, S.

4-(Ethoxycarbonylmethyl)-2-methyl-1,2,4-thiadiazolidine-3,5-dione (Compound 45)

Reagents: Ethyl isothiocyanatoacetate (0.8 ml, 6.5 mmol), 35% HCl (3.1 ml), KMnO₄ (0.5 g), methyl isocyanate (0.38 ml, 6.5 mmol).

Conditions: Room temperature, 8 h.

Isolation: filtration of reaction mixture.

Purification: recrystallization from hexane.

Yield 0.28 g (20%) as white solid; mp 67-69° C.

¹H-NMR (CDCl₃): 1.3 (t, 3H, CH₂CO₂CH₂CH₃, J=7.1 Hz); 3.2 (s, 3H, CH₃); 4.2 (c, 2H, CH₂CO₂CH₂CH₃, J=7.1 Hz); 4.4 (s, 2H, CH₂CO₂CH₂CH₃).

¹³C-NMR (CDCl₃): 14.0 (CH₂CO₂CH₂CH₃); 31.5 (CH₃); 42.7 (CH₂CO₂CH₂CH₃); 62.1 (CH₂CO₂CH₂CH₃); 152.6 (3-C=O); 166.4 (5-C=O); 166.4 (CO₂). Anal. ($C_7H_{10}N_2SO_3$) C, H, N, S.

4-(Ethoxycarbonylmethyl)-2-isopropyl-1,2,4-thiadiazolidine-3,5-dione (Compound 46)

Reagents: Ethyl isothiocyanatoacetate (0.8 ml, 6.5 mmol), 35% HCl (3.1 ml), KMnO₄ (0.5 g), isopropyl isocyanate (0.64 ml, 6.5 mmol).

Conditions: Room temperature, 9 h

Isolation: filtration of reaction mixture. .

Purification: recrystallization from hexane.

Yield: 0.48 g (30%) as white solid; mp 80-82° C.

$^1$H-NMR (CDCl$_3$): 1.3 (t, 3H, CH$_2$CO$_2$CH$_2$CH$_3$, J=7.1 Hz); 1.3 (d, 6H, CH(CH$_3$)$_2$, J=7.1 Hz); 3.8 (sp, 1H, CH(CH$_3$)$_2$, J=7.1 Hz); 4.1 (c, 2H, CH$_2$CO$_2$CH$_2$CH$_3$, J=7.1 Hz); 4.4 (s, 2H, CH$_2$CO$_2$CH$_2$CH$_3$).

$^{13}$C-NMR (CDCl$_3$): 13.6 (CH$_2$CO$_2$CH$_2$CH$_3$); 20.1 (CHCH$_3$CH$_3$); 45.1 (CHCH$_3$CH$_3$); 48.2 (CH$_2$CO$_2$CH$_2$CH$_3$); 59.2 (CH$_2$CO$_2$CH$_2$CH$_3$); 153.0 (3-C=O); 165.6 (5-C=O); 167.3 (CO$_2$). Anal. (C$_9$H$_{14}$N$_2$SO$_4$) C, H, N, S.

2-Benzoyl-4-(ethoxycarbonylmethyl)-1,2,4-thiadiazolidine-3,5-dione (Compound 47)

Reagents: Ethyl isothiocyanatoacetate (0.8 ml, 6.5 mmol), 35% HCl (3.1 ml), KMnO$_4$ (0.5 g), benzoyl isocyanate (0.81 ml, 6.5 mmol).

Conditions: Room temperature, 9 h.

Isolation: solvent evaporation.

Purification: silica gel column chromatography using AcOEt/Hexane (1:5).

Yield: 0.07 g (4%) as colorless oil.

$^1$H-NMR (CDCl$_3$): 1.26 (t, 3H, CH$_2$CO$_2$CH$_2$CH$_3$, J=7.1 Hz); 4.2 (c, 2H, CH$_2$CO$_2$CH$_2$CH$_3$, J=7.1 Hz); 4.4 (s, 2 H, CH$_2$CO$_2$CH$_2$CH$_3$); 7.4-7.7 (m, 5H, arom).

$^{13}$C-NMR (CDCl$_3$): 13.9 (CH$_2$CO$_2$CH$_2$CH$_3$); 42.3 (CH$_2$CO$_2$CH$_2$CH$_3$); 62.4 (CH$_2$CO$_2$CH$_2$CH$_3$); 127.9; 129.2; 131.7; 133.1 (C arom); 148.6 (3-C=O); 164.4 (5-C=O); 166.4 (CH$_2$CO$_2$CH$_2$CH$_3$); 165.7(CO-Ph). Anal. (C$_{13}$H$_{12}$N$_2$SO$_5$) C, H, N, S.

2-Ethyl-4-(4-nitrophenyl)-1,2,4-thiadiazolidine-3,5-dione (Compound 49)

Reagents: 4-nitrophenyl isothiocyanate (1.17 g, 6.5 mmol), 35% HCl (3.1 ml), KMnO$_4$ (0.5 g), ethyl isocyanate (0.51 ml, 6.5 mmol) in THF.

Conditions: Room temperature, 10 h.

Isolation: solvent evaporation.

Purification: silica gel column chromatography using AcOEt/Hexane (1:4).

Yield: 0.26 g (11%) as yellow solid; mp. 117-118° C.

$^1$H-NMR (CDCl$_3$): 1.34 (t, 3H, CH$_2$CH$_3$, J=7.1 Hz); 3.77 (c, 2H, CH$_2$CH$_3$, J=7.1 Hz); 7.6-8.4 (m, 5H, arom).

$^{13}$C-NMR (CDCl$_3$): 13.6 (CH$_2$CH$_3$; 40.3 (CH$_2$CH$_3$); 124.3; 127.6; 137.9; 147.1 (C, arom.); 150.9 (3-C=O); 164.8 (5-C=O). Anal. (C$_{10}$H$_9$N$_3$SO$_4$) C, H, N, S.

2-Ethyl-4-phenyl-1,2,4-thiadiazolidine-3-one-5-oxime (Compound 50)

Reagents: 5-chloro-4-phenyl-2-ethyl-3-oxo-1,2,4-thiadiazolium chloride (1.24 g, 4.5 mmol), hydroxylamine hydrochloride (0.35 g, 5 mmol), pyridine (0.8 ml, 10 mmol).

Conditions: Room temperature, 12 h.

Isolation: solvent evaporation.

Purification: silica gel column chromatography using AcOEt/Hexane (1:4) first, and then preparative centrifugal circular thin layer chromatography (CCTLC) using AcOEt/Hexane (1:3).

Yield: 0.13 g (12%) as yellow solid; mp. 115-117° C.

$^1$H-NMR (CDCl$_3$): 1.28 (t, 3H, CH$_2$CH$_3$, J=7.1 Hz); 3.64 (c, 2H, CH$_2$CH$_3$, J=7.1 Hz); 6.65 (s, 1H, N—OH); 7.24-7.50 (m, 5H, arom).

$^{13}$C-NMR (CDCl$_3$): 13.4 (CH$_2$CH$_3$); 40.2 (CH$_2$CH$_3$); 127.0; 128.6; 129.2; 133.8 (C, arom.); 152.4 (3-C=O); 153.5 (5-C=NOH). Anal. (C$_{10}$H$_{11}$N$_3$SO$_2$) C, H, N, S.

4-Benzyl-2-isopropyl-1,2,4-thiadiazolidine-3,5-dione (Compound 51)

Reagents: Benzyl isothiocyanate (0.81 ml, 6.5 mmol), 35% HCl (3.1 ml), KMnO$_4$ (0.5 g), isopropyl isocyanate (0.64 ml, 6.5 mmol).

Conditions: Room temperature, 8 h.

Isolation: solvent evaporation.

Purification: silica gel column chromatography using AcOEt/Hexane (1:3).

Yield: 0.50 g (31%) as yellow oil.

$^1$H-NMR (CDCl$_3$): 1.2 (d, 6H, CH(CH$_3$)$_2$, J=6.6 Hz); 4.7 (sp, 1H, CH(CH$_3$)$_2$, J=6.6 Hz); 4.8 (s, 2H, CH$_2$Ph); 7.2-7.4 (m, 5H, arom.).

$^{13}$C-NMR (CDCl$_3$): 21.2 ((CH$_3$)$_2$CH); 45.5 (CH(CH$_3$)$_2$); 47.0 (CH$_2$Ph); 127.8; 128.4; 128.5; 135.0 (C, arom.); 151.9 (3-C=O); 165.8 (5-C=O). Anal. (C$_{12}$H$_{14}$N$_2$SO$_2$) C, H, N, S.

2-Ethyl-4-(4-methoxyphenyl)-1,2,4-thiadiazolidine-3,5-dione (Compound 53)

Reagents: 4-Methoxyphenyl isothiocyanate (0.89 ml, 6.5 mmol), 35% HCl (3.1 ml), KMnO$_4$ (0.5 g), ethyl isocyanate (0.51 ml, 6.5 mmol).

Conditions: Room temperature, 8 h.

Isolation: solvent evaporation.

Purification: silica gel column chromatography using AcOEt/Hexane (1:4).

Yield: 0.344 g (21%) as white solid.

$^1$H-NMR (CDCl$_3$): 1.2 (t, 3H, CH$_3$CH$_2$, J=7.2 Hz); 3.6 (c, 2H, CH$_3$CH$_2$, J=7.2 Hz); 3.7 (s, 3 H, p-CH$_3$O-Ph); 6.9-7.2 (2d, 4H, arom., J=9.4 Hz).

$^{13}$C-NMR (CDCl$_3$): 14.2 (CH$_3$CH$_2$); 40.6 (CH$_3$CH$_2$); 55.8 (p-CH$_3$O-Ph); 114.7; 125.6; 128.7; 159.9 (C, arom.); 152.4 (3-C=O); 165.8 (5-C=O). Anal. (C$_{11}$H$_{12}$N$_2$SO$_3$) C, H, N, S.

2-Ethyl-4-(4-methylphenyl)-1,2,4-thiadiazolidine-3,5-dione (Compound 54)

Reagents: 4-Methylphenyl isothiocyanate (0.88 ml, 6.5 mmol), 35% HCl (3.1 ml), KMnO$_4$ (0.5 g), ethyl isocyanate (0.51 ml, 6.5 mmol).

Conditions: Room temperature, 8 h.

Isolation: solvent evaporation.

Purification: silica gel column chromatography using AcOEt/Hexane (1:4).

Yield: 0.37 g (25%) as white solid.

$^1$H-NMR (CDCl$_3$): 1.3 (t, 3H, CH$_3$CH$_2$, J=7.3 Hz); 2.4 (s, 3 H, p-CH$_3$-Ph); 3.7 (c, 2H, CH$_3$CH$_2$, J=7.3 Hz); 7.20-7.34 (m, 4H, arom.).

$^{13}$C-NMR (CDCl$_3$): 13.9 (CH$_3$CH$_2$); 21.3 (p-CH$_3$-Ph); 40.3 (CH$_3$CH$_2$); 126.8; 129.8; 129.9; 139.1 (C, arom.); 152.0 (3-C=O); 165.4 (5-C=O). Anal. (C$_{11}$H$_{12}$N$_2$SO$_2$) C, H, N, S.

(4-Bromophenyl)-2-ethyl-1,2,4-thiadiazolidine-3,5-dione (Compound 55)

Reagents: 4-Bromophenyl isothiocyanate (1.4 g, 6.5 mmol), 35% HCl (3.1 ml), KMnO$_4$ (0.5 g), ethyl isocyanate (0.51 ml, 6.5 mmol).

Conditions: Room temperature, 9 h.

Isolation: solvent evaporation.

Purification: silica gel column chromatography using AcOEt/Hexane (1:4).

Yield: 0.256 g (13%) as white solid.

$^1$H-NMR (CDCl$_3$): 1.3 (t, 3H, CH$_3$CH$_2$, J=7.2 Hz); 3.7 (c, 2H, CH$_3$CH$_2$, J=7.2 Hz); 7.3-7.6 (2 d, 4H, arom., J=8.8 Hz).

$^{13}$C-NMR (CDCl$_3$): 13.8 (CH$_3$CH$_2$); 40.4 (CH$_3$CH$_2$); 122.9; 128.5; 131.5; 132.3 (C, arom.); 151.4 (3-C=O); 164.9 (5-C=O). Anal. (C$_{10}$H$_9$N$_2$SO$_2$Br) C, H, N, S.

GSK-3 inhibition: The experiments of inhibition were also performed at variable concentrations of ATP (up to 50 µM) and in all cases the same value of IC$_{50}$ were obtained. Thus could suggest that thiadiazolinediones do not compete with ATP in the binding to GSK-3.

The first four compounds were assayed for inhibition of other enzymes.

Protein kinase A (PKA) inhibition: The potential inhibition of this enzyme is evaluated by determining the esthatmine phosphorylation by the protein kinase A (PKA). The esthatmine was purified following the procedure described by Belmont and Mitchinson (Belmont, L. D.; Mitchinson, T. J. "Identification of a protein that interact with tubulin dimers and increases the catastrophe rate of microtubule", *Cell*, 1996, 84, 623-631).

Concretely, it was used purified PKA (Sigma, catalytic subunit from bovine heart (p 2645)) and 10-15 µg of substrate (esthatmine) in a 25 µl total volume of buffer solution containing 20 µM (γ-$^{32}$P)ATP. The cAMP kinase protein (100 ng/reaction) was performed in 50 µl of 25 mM hepes, pH 7.4, 20 mM MgCl$_2$, 2 mM EGTA, 2 mM dithiothreitol, 0.5 mM Na$_3$VO$_4$. After the reaction took place, a quenching buffer was added, the reaction mixture was boiled at 100° C. during 5 minutes and the phosphorylated protein was characterized by gel electrophoresys and quantified by autoradiographia.

In these conditions none of the compounds assayed showed any inhibition of PKA.

Protein kinase C (PKC) inhibition: The potential inhibition of this enzyme is evaluated by determining the phosphorylation of the peptide PANKTPPKSPGEPAK (Woodgett, J. R. "Use of peptides for affinity purification of protein-serine kinases", *Anal. Biochem.*, 1989, 180, 237-241) by the protein kinase C (PKC) using phosphatidyl serine as stimulating agent. The method followed is the same described above for GSK-3.

Concretely, it was used PKC purified from rat brains following the method described by Walsh (Walsh, M. P.; Valentine, K. A.; Nagi, P. K.; Corruthers, C. A.; Hollenberg, M. D. *Biochem. J.*, 1984, 224, 117-127) and 1-10 mM of substrate in a total volume of 25 µl of adecuated buffer solution containing 10 µM (γ-$^{32}$P)ATP.

In these conditions none of the compounds assayed showed any inhibition of PKC.

Casein kinase 2 (CK-2) inhibition: The phosphorylating activity of this enzyme against esthatmine has been measured using CK-2 purified from bovine brains, following the method described by Alcazar (Alcazar, A.; Marín, E.; Lopez-Fando, J.; Salina, M. "An improved purification procedure and properties of casein kinase II from brain", *Neurochem. Res.*, 1988, 13, 829-836), with 3.6 µM of substrate in a total volume of 25 µl of an adequate buffer solution containing 20 µM (γ-$^{32}$P)ATP. The CK-2 assays were performed with esthatmine as substrate (see PKA determination) in 50 µl of 25 mM Hepes, pH 7.4, 20 mM MgCl$_2$, 2 mM EGTA, 2 mM dithiothreitol, 0.5 mM Na$_3$VO$_4$, and 100 ng of purified CK-2.

After the reaction took place, it was followed the same method described for PKA.

In these conditions none of the compounds assayed showed any inhibition of CK-2.

Cyclin dependent protein kinase 2 (Cdc2) inhibition: The phosphorylating activity of this enzyme against histone H1 has been measured using Cdc2 (Calbiochem) following the method described by Kobayashi (Kobayashi, H.; Stewart, E.; Poon, R. Y.; Hunt, T. "Cyclin A and cyclin B dissociate from p34cdc2 with half-times of 4 and 15 h, respectively, regardless of the phase of the cell cycle", *J. Biol. Chem.*, 1994, 269, 29153-29160), with 1 µg/µl of substrate in a total volume of 25 µl of the adequate buffer solution containing 20 µM (γ-$^{32}$P) ATP. The Cdc2 assays were performed with histone H1 as substrate (see PKA determination) in 50 µl of buffer pH 7.5, 50 mM Tris-HCl, 10 mM Cl$_2$Mg, 1 mM DTT, 1 mM EGTA, 100 µM ATP, 0.01% BRIJ-35. After the reaction took place, it was followed the same method described for PKA.

In these conditions none of the compounds assayed showed any inhibition of Cdc2.

Example 2

Analysis of the Neurites Growth After the Drug Treatment

Cells were maintained in a Dulbecco medium (DEMEM) with a 10% fethal bovine serum, glutamine (2 mM) and antibiotics. For the analysis of the potential GSK-3 inhibition in vivo, mice neuroblastoms N$_2$A cultures (Garcia-Perez, J.; Avila, J.; Diaz-Nido, J. "Lithium induces morphological differentiation of mouse neuroblastoma", *J. Neurol. Res.*, 1999, 57, 261-270) were used. The test compounds were added to these cells cultures. This cell line has the particularity of expressed a certain kind of neuronal phenotype (neuritic extensions) after the addition of lithium chloride (10 mM), a known GSK-3 inhibitor. After 2-3 days of culture, it was check the effect of the tested compounds gathered in table I. It was observed that the generation of neuritic extension in the same extension than when lithium was added. That fact confirms the in vivo GSK-3 inhibition of the compounds of the invention.

Example 3

Cell Cycle Blockade

In parallel, the potential interference of these compounds with the cell cycle was studied on N$_2$A cells. The cell culture was maintained in a Dulbecco medium (DEMEM) with a 10% fethal bovine serum, glutamine (2 mM) and antibiotics.

The first four compounds of general formula (I) gathered in Table 3 were assayed in the described conditions and shown ability to inhibit the cell cycle at an inhibitor concentration comprised between 100 nM and 1 µM. The cellular blockade was initially observed at concentrations comprised between 100-200 nM and was totally effective at 1 µM.

The tested compounds was non toxic in stationary fibroblast culture MRC-5 after 10 days of continue exposure to the inhibitors.

Example 4

GSK-3 Inhibition of Further Compounds

GSK-3 Inhibition Data

TABLE 4

| Family | Compound | | $IC_{50}$ (μM) |
|---|---|---|---|
| A | [structure] | 1-A | >100 |
| B | [structure] | 1-B | 12 |
| C | [structure] | 1-C | >100 |
| D | [structure] | R = H (1-D)<br>R = $CH_2Ph$ (2-D)<br>R = Me (3-D) | 6<br>1<br>5 |
| E | [structure] | R = H; X, Y = O (1-E)<br>R = $CH_2Ph$; X, Y = O (2-E)<br>R = $CH_2Ph$; X = O; Y = H (3-E) | >100<br>>100<br>>100 |
| F | [structure] | R = H (1-F)<br>R = $CH_2Ph$ (2-F) | >100<br>>100 |
| G | [structure] | R = H (1-G)<br>R = Me (2-G)<br>R = $CH_2CO_2H$ (3-G)<br>R = $CH_2Ph$ (4-G)<br>R = $CH_2CH_2Ph$ (5-G)<br>R = $CH_2COPh$ (6-G) | >100<br>>100<br>>100<br>25<br>35<br>50 |
| H | [structure] | R = H (1-H)<br>R = Me (2-H) | >100<br>>100 |

Detailed Synthesis of Some of the Compounds Depicted in Table 4 (Families A-H)

Synthesis of the Compounds of Family D:

N-Benzylmaleimide (compound 2-D): described in Walker, M. A., *Tetrahedron Lett.*, 1994, 35, 665-668.

Synthesis of the Compounds of Family G:

(4-oxo-2-thioxo-thiazolidin-3-yl)-acetic acid (compound 3-G): Girard, M. L.; Dreux, C., *Bull. Soc. Chim. Fr,* 1968, 3461-3468.

3-Benzyl-2-thioxo-thiazolidin4-one (Compound 4-G)

Reagents: Rhodanine (53 mg, 0.4 mmol), triethylamine (0.05 ml) and benzyl bromide (68 mg, 0.4 mmol) in 25 ml of acetone.

Conditions: Refluxed for 6 h.

Isolation: Add water and extract with ethyl acetate (3×5 ml).

Purification: preparative centrifugal circular thin layer chromatography (CCTLC) using $CH_2Cl_2$/Hexane (2:1).

Yield: 10 mg (10%) as yellow oil.

$^1$H-NMR (CDCl$_3$): 3.9 (s, 2H); 5.2 (s, 2H, $CH_2Ph$); 7.3-7.4 (m, 5H, arom).

$^{13}$C-NMR (CDCl$_3$): 35.4 ($CH_2$); 47.6 ($CH_2Ph$); 128.2; 128.6; 129.1; 134.7 (C arom); 153.8 (C=O); 173.8 (C=S). Anal. ($C_{10}H_9NS_2O$) C, H, N, S.

An alternative method for the synthesis of this compound is described in *J. Parkt. Chem.*, 1910, 81, 456, the contents of which are incorporated herein by reference thereto.

3-Phenethyl-2-thioxo-thiazolidin-4-one (Compound 5-G)

Reagents: Rhodanine (133 mg, 1 mmol), triethylamine (0.14 ml) and phenethyl bromide (0.14 ml, 1 mmol) in 25 ml of acetone.

Conditions: Refluxed for 12 h.

Isolated: Add water and extract with ethyl acetate (3×10 ml).

Purification: preparative centrifugal circular thin layer chromatography (CCTLC) using $CH_2Cl_2$/Hexane (2:1).

Yield: 10 mg (4%) as yellow oil.

$^1$H-NMR (CDCl$_3$): 2.9 (t, 2H, $CH_2CH_2Ph$, J=8.1), 3.9 (s, 2H); 4.2 (s, 2H, $CH_2CH_2Ph$, J=8.1); 7.4-7.9 (m, 5H, arom).

$^{13}$C-NMR (CDCl$_3$): 32.6 ($CH_2CH_2Ph$); 35.3 ($CH_2$); 45.7 ($CH_2CH_2Ph$); 126.8; 128.6; 128.6; 137.4 (C, arom); 173.5 (C=O); 200.9 (C=S). Anal. ($C_{11}H_{11}NS_2O$) C, H, N, S.

An alternative method for the synthesis of this compound is described in: Buck, Leonard, *J. Am. Chem. Soc.*, 1931, 53, 2688-2690, the contents of which are incorporated herein by reference thereto.

3-Phenacyl-2-thioxo-thiazolidin-4-one (Compound 6-G)

Reagents: Rhodanine (133 mg, 1 mmol), $K_2CO_3$ (excess) and acetophenone bromide (199 mg, 1 mmol) in 25 ml of acetone.

Conditions: Stirred at room temperature for 3 h.

Isolation: Filtration of the carbonate and evaporation of the solvent to dryness in vacuo.

Purification: preparative centrifugal circular thin layer chromatography (CCTLC) using $CH_2Cl_2$.

Yield: 38 mg (15%) as brown oil.

$^1$H-NMR (CDCl$_3$): 3.9 (s, 2H); 4.2 (s, 2H, $CH_2COPh$); 7.4-7.9 (m, 5H, arom).

$^{13}$C-NMR (CDCl$_3$): 37.6 ($CH_2$); 45.3 ($CH_2COPh$); 128.6; 128,7; 133.5; 135.3 (C, arom); 170.5 (C=O); 194.1 ($CH_2COPh$); 197.6 (C=S). Anal. ($C_{11}H_9NS_2O_2$) C, H, N, S.

Further compounds of formula (III) have been synthesised and their GSK-3 inhibition tested. These compounds are listed in Tables 4a and 4b below.

TABLE 4a

This lists further compounds of Family D in Table 4 above, ie those compounds of formula:

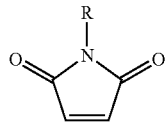

wherein R is as listed in the Table.

| Compound No. | R | GSK-3β IC$_{50}$ (μM) |
|---|---|---|
| 4-D | (CH$_2$)$_2$Ph | 2 |
| 5-D | (CH$_2$)$_3$Ph | 3 |
| 6-D | (CH$_2$)$_5$Ph | 3 |
| 7-D | p-OCH$_3$—Bn | 2.5 |
| 8-D | p-OCH$_3$—(CH$_2$)$_2$Ph | 3 |
| 9-D | CH$_2$CO$_2$Et | 3 |

General Method for the Synthesis of N-alkyl-maleimides

This method is described in: Walker, M. A., *Tetrahedron Lett.*, 1995, 35, 665-668, the contents of which are incorporated herein by reference thereto.

A 50 ml round bottom flask was charged with Ph$_3$P to which was added 25 ml of dry THF. The resulting clear solution was cooled to −70° C. under a nitrogen atmosphere. DIAD or DEAD, depending on the case, was added over 2-3 min. The yellow reaction mixture was stirred 5 min after which the corresponding alkyl alcohol was added over 1 min and stirred for 5 min. Maleimide was then added to the reaction mixture as solid. The resulting suspension was allowed to remain at −70° C. for 5 min, during which time most of the maleimide dissolved. The cooling bath was then removed, and the reaction was stirred overnight at ambient temperature. The solvent was evaporated to dryness in vacuo and the residue purified by silica gel column chromatography using as eluant mixtures of solvents in the proportions indicated for each particular case.

N-phenethylmaleimide (compound 4-D): Walker, M. A., *Tetrahedron Lett.*, 1995, 35, 665-668.

N-(3-phenylpropyl)maleimide (Compound 5-D)

Reagents: Ph$_3$P (0.65 g, 2.5 mmol), DIAD (0.5 ml, 2.5 mmol), 3-phenyl-1-propanol (0.48 ml, 3.75 mmol) and maleimide (0.24 g, 2.5 mmol).

Conditions: Room temperature, overnight.

Purification: silica gel column chromatography using AcOEt/Hexane (1:4).

Yield: 0.20 g (37%) as white solid; mp 79-80° C.

$^1$H-NMR (CDCl$_3$): 1.92 (q, 2H, CH$_2$CH$_2$CH$_2$Ph, J=7.1 Hz); 2.60 (t, 2H, CH$_2$CH$_2$CH$_2$Ph, J=7.1 Hz); 3.55 (t, 2H, CH$_2$CH$_2$CH$_2$Ph, J=7.1 Hz); 6.27 (d, 2H, CH=CH, J=6.4 Hz); 7.12-7.28 (m, 5H, arom).

$^{13}$C-NMR (CDCl$_3$): 29.6 (CH$_2$_CH$_2$CH$_2$Ph); 32.8 (CH$_2$CH$_2$CH$_2$Ph); 37.4 (CH$_2$CH$_2$CH$_2$Ph); 125.8; 128.1; 128.2; 140.7 (C, arom); 133.7 (C=C); 170.6 (C=O) Anal. (C$_{13}$H$_{13}$NO$_2$) C, H, N, S.

N-(5-phenylpentyl)maleimide (Compound 6-D)

Reagents: Ph$_3$P (0.65 g, 2.5 mmol), DIAD (0.5 ml, 2.5 mmol), 5-phenyl-1-pentanol (0.63 ml, 3.75 mmol) and maleimide (0.24 g, 2.5 mmol).

Conditions: Room temperature, overnight.

Purification: silica gel column chromatography using AcOEt/Hexane (1:4).

Yield: 0.32 g (52%) as white-yellow solid; mp 49-51° C.

$^1$H-NMR (CDCl$_3$): 1.20-138 (m, 2H, CH$_2$CH$_2$CH$_2$CH$_2$_CH$_2$Ph); 1.52-2.02 (m, 4H, CH$_2$CH$_2$CH$_2$CH$_2$CH$_2$Ph); 2.57 (t, 2H, CH$_2$CH$_2$CH$_2$CH$_2$_CH$_2$Ph, J=7.3 Hz); 3.5 (t, 2H, CH$_2$CH$_2$CH$_2$CH$_2$CH$_2$Ph, J=7.3 Hz); 6.65 (d, 2H, CH=CH, J=6.4 Hz); 7.11-7.28 (m, 5H, arom).

$^{13}$C-NMR (CDCl$_3$): 25.9 (CH$_2$CH$_2$CH$_2$_CH$_2$CH$_2$Ph); 28.0 (CH$_2$CH$_2$CH$_2$_CH$_2$CH$_2$Ph); 30.6 (CH$_2$CH$_2$CH$_2$CH$_2$_CH$_2$Ph); 35.4 (CH$_2$CH$_2$CH$_2$CH$_2$_CH$_2$Ph); 37.3 (CH$_2$CH$_2$CH$_2$CH$_2$CH$_2$Ph); 125.4; 127.9; 128.0; 142.0 (C, arom); 133.6 (C=C); 170.5 (C=O) Anal. (C$_{15}$H$_{17}$NO$_2$) C, H, N, S.

N-(p-methoxybenzyl)maleimide (Compound 7-D)

Reagents: Ph$_3$P (1.31 g, 5 mmol), DEAD (0.8 ml, 5 mmol), p-methoxybenzyl alcohol (0.93 ml, 7.5 mmol) and maleimide (0.48 g, 5 mmol).

Conditions: Room temperature, overnight.

Purification: silica gel column chromatography using AcOEt/Hexane (1:3).

Yield: 0.50 g (46%) as white solid; mp. 99-102° C.

$^1$H-NMR (CDCl$_3$): 3.74 (s, 3H, OCH$_3$); 4.58 (s, 2H, CH$_2$Ph); 6.65 (d, 2H, CH=CH, J=6.4 Hz); 6.8-7.2 (m, 4H, arom).

$^{13}$C-NMR (CDCl$_3$): 40.4 (CH$_2$Ph-OCH$_3$); 54.8 (—OCH3); 113.6; 128.2; 129.5; 158.8 (C, arom); 133.8 (C=C); 170.1 (C=O) Anal. (C$_{12}$H$_{11}$NO$_3$) C, H, N, S.

N-(p-Methoxyphenethyl)maleimide (Compound 8-D)

Reagents: Ph$_3$P (1.31 g, 5 mmol), DEAD (0.8 ml, 5 mmol), p-methoxyphenethyl alcohol (1.2 g, 7.5 mmol) and maleimide (0.48 g, 5 mmol).

Conditions: Room temperature, overnight.

Purification: silica gel column chromatography using AcOEt/Hexane (1:5).

Yield: 0.71 g (60%) as yellow solid; mp. 79-81° C.

$^1$H-NMR (CDCl$_3$): 2.80 (m, 2H, CH$_2$CH$_2$Ph); 3.70 (m, 2H, CH$_2$CH$_2$Ph); 3.75 (s, 3H, OCH$_3$); 6.63 (d, 2H, CH=CH, J=6.4 Hz); 6.8-7.1 (m, 4H, arom).

$^{13}$C-NMR (CDCl$_3$): 33.5 (CH$_2$CH$_2$Ph-OCH$_3$); 39.2 (CH$_2$CH$_2$Ph-OCH$_3$); 55.5 (—OCH$_3$); 114.0; 129.7; 129.9; 158.4 (C, arom); 133.9 (C=C); 170.5 (C=O). Anal. (C$_{13}$H$_{13}$NO$_3$) C, H, N, S.

N-(Ethoxycarbonylmethyl)maleimide (Compound 9-D)

Reagents: Ph$_3$P (1.31 g, 5 mmol), DEAD (0.8 ml, 5 mmol), ethyl glycollate (0.71 ml, 7.5 mmol) and maleimide (0.48 g, 5 mmol).

Conditions: Room temperature, overnight.

Purification: silica gel column chromatography using AcOEt/Hexane (1:3).

Yield: 0.30 g (33%) as colourless oil.

$^1$H-NMR (CDCl$_3$): 1.25 (t, 3H, CH$_2$CO$_2$CH$_2$CH$_3$, J=7.1 Hz); 4.20 (c, 2H, CH$_2$CO$_2$CH$_2$CH$_3$, J=7.1 Hz); 4.24 (s, 2H, CH$_2$CO$_2$CH$_2$CH$_3$); 6.76 (d, 2H, CH=CH, J=6.4 Hz).

$^{13}$C-NMR (CDCl$_3$): 13.7 (CH$_2$CO$_2$CH$_2$CH$_3$); 38.4 (CH$_2$CO$_2$CH$_2$CH$_3$); 61.5 (CH$_2$CO$_2$CH$_2$CH$_3$); 134.3 (C=C); 166.9 (CO$_2$); 169.6 (C=O). Anal. (C$_8$H$_9$NO$_4$) C, H, N, S.

TABLE 4b

This lists the activity of further compounds of Family G in Table 4 above, ie those compounds of formula:

| Compound No. | R | GSK-3β IC$_{50}$ (μM) |
|---|---|---|
| 7-G | NH$_2$ | >100 |
| 8-G | CH$_2$(4-MeO-Ph) | 65 | wherein R is as listed in the table.

GSK-3 inhibitors: For compounds belonging to family D, the GSK-3 inhibition experiments were also performed at variable concentrations of ATP (up to 50 μM) and in all cases the same value of IC$_{50}$ were obtained. Thus could suggest that these compounds do not compete with ATP in the binding to GSK-3.

Example 5

Cell Cycle Blockade

The IC$_{50}$ for some of the compounds tested in N$_2$A cell cultures are gathered in Table 5 below.

TABLE 5

(II)

| R$^a$ | R$^b$ | X | Y | IC$_{50}$ (μM) |
|---|---|---|---|---|
| CH$_2$Ph | Me | O | O | 4-8 |
| Et | Me | O | O | 40-100 |
| Et | nPr | O | O | 5-10 |
| Et | cyclohexyl | O | O | 6-9 |
| Ph | Me | O | O | 4-7 |
| CH$_2$CO$_2$Et | Me | O | O | 1-2 |

TABLE 5-continued (II)

| R$^a$ | R$^b$ | X | Y | IC$_{50}$ (μM) |
|---|---|---|---|---|
| 4-OMePh | Me | O | O | 1-2 |
| CH$_2$Ph | Et | O | O | 4-7 |
| CH$_2$Ph | CH$_2$Ph | O | O | 2-3 |
| Et | Et | O | O | 30-80 |
| CH$_2$Ph | CH$_2$Ph | O | S | 1-2 |
| Ph | Ph | O | S | 4-8 |

The invention claimed is:

1. A compound having formula (II):

(II)

wherein
  R$^a$ is benzyl;
  R$^b$ is alkyl; and
  X and Y are both O; or a pharmaceutically acceptable salt thereof.

2. The compound of claim 1, wherein R$^b$ is n-propyl, n-butyl, t-butyl, or n-pentyl.

3. The compound of claim 1, wherein R$^b$ is methyl.

4. The compound of claim 1, wherein R$^b$ is ethyl.

5. The compound of claim 1, wherein R$^b$ is i-propyl.

6. A pharmaceutical composition comprising a compound having formula (II) or a pharmaceutically acceptable salt thereof:

(II)

wherein
  R$^a$ is benzyl;
  R$^b$ is alkyl; and
  X and Y are both O; and a pharmaceutically acceptable carrier or diluent.

7. The composition of claim 6, wherein R$^b$ is n-propyl, n-butyl, t-butyl, or n-pentyl.

8. The composition of claim 6, wherein R$^b$ is methyl.

9. The composition of claim 6, wherein R$^b$ is ethyl.

10. The composition of claim 6, wherein R$^b$ is i-propyl.

* * * * *